United States Patent
Sasaki et al.

(10) Patent No.: US 9,340,814 B2
(45) Date of Patent: May 17, 2016

(54) METHOD FOR PRODUCING A RECOMBINANT PROTEIN USING A CELL LINE ADAPTED TO A PROTEIN-FREE AND LIPID-FREE MEDIUM

(71) Applicants: Kyokuto Pharmaceutical Industrial Co., Ltd., Tokyo (JP); National Institute for Materials Science, Ibaraki (JP)

(72) Inventors: Tetsuji Sasaki, Ibaraki (JP); Akiyoshi Taniguchi, Ibaraki (JP)

(73) Assignees: Kyokuto Pharmaceutical Industrial Co., Ltd., Tokyo (JP); National Institute for Materials Science, Ibaraki (JP)

( * ) Notice: Subject to any disclaimer, the term of this patent is extended or adjusted under 35 U.S.C. 154(b) by 0 days.

(21) Appl. No.: 14/186,881

(22) Filed: Feb. 21, 2014

(65) Prior Publication Data

US 2015/0044719 A1 Feb. 12, 2015

(30) Foreign Application Priority Data

Aug. 8, 2013 (JP) .................................. 2013-164837

(51) Int. Cl.

| C12P 21/06 | (2006.01) |
|---|---|
| C12P 21/04 | (2006.01) |
| C12N 5/07 | (2010.01) |
| C12N 5/00 | (2006.01) |
| C12P 21/00 | (2006.01) |
| C12N 5/071 | (2010.01) |

(52) U.S. Cl.
CPC ................. *C12P 21/00* (2013.01); *C12N 5/005* (2013.01); *C12N 5/0682* (2013.01); *C12N 2500/25* (2013.01); *C12N 2500/46* (2013.01); *C12N 2510/02* (2013.01)

(58) Field of Classification Search
CPC ........ C12P 21/00; C12N 5/00; C12N 5/0682; C12N 2500/25; C12N 2500/46; C12N 2510/02
See application file for complete search history.

(56) References Cited

U.S. PATENT DOCUMENTS

| 5,316,938 A | * | 5/1994 | Keen et al. ................... 435/404 |
| 6,100,061 A | * | 8/2000 | Reiter et al. ................. 435/69.1 |

OTHER PUBLICATIONS

Sigma Product Brochure: Dulbecco's Modified Eagle's Medium/Ham's Nutrient Mixture F-12 (DMEM/F12) Formulation: retrieved from the internet Jun. 30, 2015:http://www.sigmaaldrich.com/life-science/cell-culture/learning-center/media-formulations/dme-f12.html.*

(Continued)

*Primary Examiner* — Reza Ghafoorian
(74) *Attorney, Agent, or Firm* — Osha Liang LLP

(57) ABSTRACT

A method for producing a recombinant protein includes steps of: (a) culturing a transformed cell in a protein-free and lipid-free medium containing no exogenous growth factors, in which the transformed cell is produced by transfecting a cell of a cell line derived from Chinese Hamster Ovary (CHO) cells, the cell line is adapted to a protein-free and lipid-free medium, and the cell is capable of proliferating in a suspended state in a protein-free and lipid-free medium containing no exogenous growth factors, with a vector containing a gene coding for the protein to be produced under the control of a promoter operable in the cell, and (b) recovering the protein produced by the transformed cell.

20 Claims, 17 Drawing Sheets

A: Process for adaptation of a cell line adapted to a DMEM medium
(DMAd (Dulbecco's Modified Eagle's MEM Adapted) CHO cells)

B: Process for adaptation of a cell line adapted to a NPL medium
(NPLAd (No-Protein, No-Lipid Medium Adapted) CHO cells)

(56) References Cited

OTHER PUBLICATIONS

Sunstrom, Noelle-Anne S., et al., "Insulin-Like Growth Factor-I and Transferrin Mediate Growth and Survival of Chinese Hamster Ovary Cells"; Biotechnol. Prog. 2000, vol. 16; 2000 American Chemical Society and American Institute of Chemical Engineers, published on Web Sep. 20, 2000; 10.1021/bp000102t CCC; pp. 698-702.

Kagawa, Yasuo, et al., Mitochondria of Mouse Fibroblasts, L-929, Cultured in a Lipid- and Protein-Free Chemically Defined Medium; The Journal of Biochemistry, vol. 65, No. 6, 1969; pp. 799-808.

Kagawa, Yasuo, et al., "Absence of Essential Fatty Acids in Mammalian Cell Strains Cultured in Lipid- and Protein-Free Chemically Defined Synthetic Media"; The Journal of Biochemistry, vol. 68, No. 1, 1970; pp. 133-136.

Sasaki, Tetsuji, et al., "Development of a Non-protein and Lipid Medium Adopted Cell Line for Biopharmaceutical Recombinant Protein Expression"; the Open Biotechnology Journal, vol. 7, Feb. 22, 2013; ISSN: 1874-0707; DOI: 10.2174/1874070701307010001; pp. 1-6.

Lundholm, Beverly, et al., "Plaque Production by the Polyoma Virus"; Letters to the Editors, School of Veterinary Medicine, University of California, Davis, California, pp. 396-397.

Eagle, Harry, "Amino Acid Metabolism in Mammalian Cell Cultures"; Science, vol. 130; pp. 432-437, Aug. 21, 1959.

Chun, Chung, et al., "Application of Factorial Design to Accelerate Identification of CHO Growth Factor Requirements"; Biotechnol. Prog., vol. 19, 2003; 2003 American Chemical Society and American Institute of Chemical Engineers published on Web Dec. 28, 2002, 10.1021/bp025575+ CCC; pp. 52-57.

Rosenfeld, Louis, "Insulin: Discovery and Controversy"; Clinical Chemistry, vol. 48, No. 12, 2002; pp. 2270-2288.

Bremer, Eric G., et al., "Ganglioside-mediated Modulation of Cell Growth, Specific Effects of GM3 on Tyrosine Phosphorylation of the Epidermal Growth Factor Receptor"; The Journal of Biological Chemistry, by the American Society of Biological Chemists, Inc., vol. 261, No. 5, Issue of Feb. 15, 1986; pp. 2434-2440.

Ji, Li, et al., "The hydrolysis of cell surface glycosphingolipids by endoglycoceramidase reduces epidermal growth factor receptor phosphorylation in A431 cells"; Glycobiology, vol. 5, No. 3, 1995; pp. 343-350.

Li, Ruixiang, et al., "Cellular Gangliosides Promote Growth Factor-induced Proliferation of Fibroblasts"; The Journal of Biological Chemistry, by the American Society for Biochemistry and Molecular Biology, Inc., vol. 275, No. 44, Issue of Nov. 3, 2000; doi: 10.1074/jbc.M906368199 originally published online Jun. 19, 2000; pp. 34213-34223.

Tagami, Seiichi, et al., "Ganglioside GM3 Participates in the Pathological Conditions of Insulin Resistance"; The Journal of Biological Chemistry, by the American Society for Biochemistry and Molecular Biology, Inc., vol. 277, No. 5, Issue of Feb. 1, 2002; doi: 10.1074/jbc.M103705200 originally published online Nov. 13, 2001; pp. 3085-3092.

Sasaki, Tetsuji, Deposit of Microorganism, NPLAd001, NITE BP-01641, Budapest Treaty on the International Recognition of the Deposit of Microorganisms for the Purposes of Patent Procedure Receipt in the Case of an Original Deposit issued pursuant to Rule 7.1 by the International Depositary of Authority, by the NITE Patent Microorganisms Depositary, National Institute of Technology and Evaluation, Chiba, Japan (1 page).

Sasaki, Tetsuji, Viability Statement, Budapest Treaty on the International Recognition of the Deposit of Microorganisms for the Purposes of Patent Procedure issued pursuant to Rule 10.2 by the International Depositary Authority, by the NITE Patent Microorganisms Depositary, National Institute of Technology and Evaluation, Chiba, Japan (1 page).

Inokuchi, Jin-ichi, "Involvement of micro-and ganglioside GM3 domain increased expression in insulin resistance expression of adipocyte"; Obesity Research, 2006, vol. 12; pp. 260-262, with English translation (9 pages).

Shvartsman, S. Y., "Autocrine loops with positive feedback enable context-dependent cell signaling"; Am. J. Physiol. Cell Physiol. vol. 282: 2002, first published Oct. 17, 2001 by the American Physiological Society, http://www.ajpcell.org; 10.1152/ajpcell.00260.2001; pp. C545-0559.

DeWitt, Ann E., et al., "Quantitative analysis of the EGF receptor autocrine system reveals cryptic regulation of cell response by ligand capture"; Journal of Cell Science 114, , Mar. 29, 2001, The Company of Biologists Ltd., pp. 2301-2313.

Pak, S.C.O., et al., "Super-CHO—A cell line capable of autocrine growth under fully defined protein-free conditions"; Cytotechnology, vol. 22, 1996, Kluwer Academic Publishers, The Netherlands; pp. 139-146.

Balbis, Alejandro, et al., "Compartmentalization of EGFR in Cellular Membranes: Role of Membrane Rafts"; Journal of Cellular Biochemistry, vol. 109, 2010; pp. 1103-1108.

\* cited by examiner

A: Process for adaptation of a cell line adapted to a DMEM medium (DMAd (Dulbecco's Modified Eagle's MEM Adapted) CHO cells)

B: Process for adaptation of a cell line adapted to a NPL medium (NPLAd (No-Protein, No-Lipid Medium Adapted) CHO cells)

METHOD FOR PRODUCING A RECOMBINANT PROTEIN USING A CELL LINE ADAPTED TO A PROTEIN-FREE AND LIPID-FREE MEDIUM

CROSS REFERENCE TO RELATED APPLICATIONS

This claims priority of Japanese Patent Application No. 2013-164837, filed on Aug. 8, 2013, the disclosure of which is incorporated by reference in its entirety.

TECHNICAL FIELD

The present invention relates to a novel cultured cell line adapted to a medium substantially free of proteins or lipids, a method for producing the cell line, a medium for culturing the cell line, and a use of the cell line for producing a recombinant protein.

BACKGROUND ART

The share of biopharmaceuticals has been rapidly increasing in a medicinal market. Among biopharmaceuticals, remarkably increasing have been recombinant protein formulations such as enzymes, hormones, antibodies, growth factors, and blood coagulation factors. For stable supplies of these pharmaceuticals, establishment of a system for producing a recombinant protein, which is safe, low-cost and efficient, is desired.

Recombinant proteins have been conventionally expressed using *Escherichia coli*, etc. because of the productivity and efficiency. However, the expression systems of *E. coli* have problems that it is difficult to reproduce the conformation of a protein and that a post-translational modification such as glycosylation modification cannot be achieved. Thus, many of those recombinant protein formulations each comprising a cytokine, an enzyme, an antibody drug, or the like, which involves its conformation or the post-translational modification for its activity, are produced using Chinese Hamster Ovary (CHO) cells.

The expression systems using CHO cells also involve problems. Until recent years, a serum or a biological material derived from a heterologous animal has been used for culturing CHO cells. However, the use of the serum or the biological material derived from the heterologous animal causes problems about safety such as a risk of infection of a virus originated from an animal and an allergy due to a heterologous animal antigen. Further, a problem concerning stability, such as a lot-to-lot variability, is also caused by using biological materials. Therefore, chemically defined media (synthetic media) have been developed, in which media components produced by chemical syntheses or recombinant techniques are used instead of biological materials such as a serum (Non-patent Literature 1: Sunstrom, et al., 2000). However, those components produced by chemical syntheses or recombinant techniques, especially growth factors, are expensive and unstable. Thus, it is desirable for industrial production to conduct culture without adding such substances or growth factors.

An adapted culture method, in which cells are gradually adapted to an environment which is free of materials derived from biologics or growth factors, is an approach to eliminate those factors from CHO cell culture. It has been reported for a long time that cells have an ability to adapt to an environment and can be adapted to an environment with only minimum essential nutrients by spending time on adaptation (Non-patent Literature 2: Kagawa, et al., 1969; Non-patent Literature 3: Kagawa, et al., 1970). In a protein expression system, when a protein of interest is expressed by transfecting the CHO cells with a vector carrying cDNA of the protein, a drug resistant gene is used in the transfection in order to select cells carrying the gene of interest. If any transfection is carried out in addition to transfection for introducing the gene for the protein of interest, a selection method comes to be limited. Thus, it is desirable not to carry out additional transfection. In the adapted culture method, it is unnecessary to perform an additional manipulation for gene modification such as gene introduction, because cells themselves are being adapted to the environment. In this meaning, the adapted culture method has a high flexibility in terms of introduction of the gene of interest. However, the adapted culture method is time-consuming and labor-intensive, and has a low success rate. Thus, this method has not been tried in order to obtain adapted cells derived from the CHO cells having high productivity.

Further, the CHO cells also involve other problems. The CHO cells are inherently adherent cells and therefore they are not suitable for tank culture by using, e.g., a bioreactor, which is used in large-scale productions of materials for industrial use. Adherent cells require a large cell-adhering surface area because they propagate while adhering to a vessel wall. To ensure such large adhering area, a high-density culture apparatus of a layered or hollow fiber type, or an adherent carrier such as a micro-carrier, is used, which causes problems such as complication of the culture apparatus and increase in production costs. Furthermore, to suspend the cells, a carrier or a flotation agent such as a surfactant may be used. Such carrier increases the costs for production. On the other hand, surfactants are cytotoxic and often exert toxicity to cells. Further, those surfactants must be removed as impurities upon purification of the product, and may also inhibit the purification. Therefore, it has been desired to suspend the CHO cells without using such flotation agents.

PRIOR-ART LITERATURES

Non-Patent Literatures

[Non-patent Literature 1] Sunstrom N A, Gay R D, Wong D C, Kitchen N A, DeBoer L, Gray P P. Insulin-Like Growth Factor-I and Transferrin Mediate Growth and Survival of Chinese Hamster Ovary Cells. Biotechnol Prog., 2000; 16: 698-702.

[Non-patent Literature 2] Kagawa Y, Takaoka T, Katsuta H. Mitochondria of mouse fibroblasts, L-929, cultured in a lipid- and protein-free chemically defined medium. J. Biochem., 1969; 65: 799-808.

[Non-patent Literature 3] Kagawa Y, Takaoka T, Katsuta H. Absence of essential fatty acids in mammalian cell strains cultured in lipid- and protein-free chemically defined synthetic media. J. Biochem., 1970; 68: 133-6.

SUMMARY OF INVENTION

Problem to be Solved by Invention

The present invention has been attained in view of the above circumstances, and aims to provide a CHO-derived cell line which is free of safety concerns, can be stably used for production of recombinant proteins, can proliferate in a suspended state, and can be cultured at low costs. In other words, the invention aims to provide a CHO cell line adapted to a protein-free and lipid-free medium, which cell line highly proliferates independent of materials derived from biologics or expensive and unstable factors. The present invention further aims to provide a method for adapting CHO cells by using a protein-free and lipid-free medium, a medium to be used for the method, and so on.

Means for Solving Problems

The present inventor has successfully established a CHO cell line that has adapted to a protein-free and lipid-free medium, which is free of proteinaceous biological materials or growth factors, lipids, or the like, by using an adapted culture method. Accordingly, the present invention provides followings:
[1] A method for producing a recombinant protein comprising steps of:
(a) culturing a transformed cell in a protein-free and lipid-free medium comprising no exogenous growth factors, wherein the transformed cell was produced by transfecting a cell of a cell line derived from Chinese Hamster Ovary (CHO) cells, the cell line being adapted to a protein-free and lipid-free medium, and the cell being able to proliferate in a suspended state in a protein-free and lipid-free medium comprising no exogenous growth factors, with a vector comprising a gene coding for the protein to be produced under the control of a promoter operable in the cell, and
(b) recovering the protein produced by the transformed cell;
[2] The method as described in said item [1], wherein the cell line has been deposited under Accession number NITE P-01641;
[3] The method as described in said item [1] or [2], wherein the protein-free and lipid-free medium used in the step (a) of culturing the transformed cell is a medium characterized by comprising putrescine, thymidine, hypoxanthine, and monoethanolamine, in a DMEM medium modified so as to contain glucose in an amount of 3 to 5 times of the usual amount, and by comprising no exogenous growth factors;
[4] The method as described in said items [3], wherein the protein-free and lipid-free medium used in the step (a) of culturing the transformed cell is a protein-free and lipid-free medium comprising 2000 to 5000 mg/L of glucose, 0.001 to 2 mg/L of putrescine, 0.01 to 1 mg/L of thymidine, 0.1 to 10 mg/L of hypoxanthine, and 0.1 to 5 mg/L of monoethanolamine;
[5] The method as described in any one of said items [1] to [4], wherein the protein-free and lipid-free medium used in the step (a) of culturing the transformed cell is a protein-free and lipid-free medium further comprising 1 to 20 mg/L of insulin and/or 0.1 to 10 mg/L of ganglioside GM3;
[6] The method as described in any one of said items [1] to [5], wherein the transformed cell had been cultured in a protein-free and lipid-free medium comprising insulin and ganglioside GM3 before it was subjected to the transformation; and
[7] The method as described in any one of said items [1] to [6], wherein the transformed cell had been cultured in a protein-free and lipid-free medium comprising insulin and ganglioside GM3, and thereafter subjected to the transfection in a protein-free and lipid-free medium comprising no GM3.

Effects of Invention

The present invention provides a CHO cell line adapted to a protein-free and lipid-free medium, which can proliferate in a suspended state independent of materials derived from biologics or expensive and unstable factors. The cell line adapted to a protein-free and lipid-free medium according to the present invention can be cultured in a suspended state by using a common culture apparatus for floating cells, e.g., one for spin culture or another one for high-density culture of a bioreactor type, without use of a flotation agent such as a surfactant. Further, it has been demonstrated that the suspended form of cells is not due to a deficiency of their extracellular matrix (ECMs) or is not due to irreversible morphological change associated with genetic mutation. Therefore, the adapted cell line of the present invention has morphology which enables a large-scale production by a tank culture. Further, the present cell line is a stable one without any mutation and is a safe and stable cell line desirable for production systems for biopharmaceuticals.

The cells of the adapted cell line of the present invention show a proliferative property that depends on epidermal growth factor (EGF), which is produced by the cells themselves, i.e., by an autocrine action, but not on the addition of exogenous growth factors. By inducing a lipid raft formation in a cell membrane by supplying insulin and/or GM3 ganglioside to a medium, the cells of the adapted cell line of the present invention show a proliferative property that is the same or more than the proliferative property of the original CHO cells.

Also, the cells of the adapted cell line of the present invention show a production efficiency of a recombinant protein, which is more excellent than that of the original CHO cells. Therefore, by using the adapted cell line of the present invention, it is possible to produce a desired recombinant protein efficiently, thereby the productivities of biopharmaceuticals can be increased. By using the adapted cell line of the present invention, biopharmaceuticals can be produced in a safer, less expensive, and more stable manner.

The process for producing the adapted cells of the present invention does not require any special apparatus, and it enables production of the adapted cells that can be cultured in a suspended state with a high reproducibility. Further, the medium of the present invention is advantageous because it is substantially free of proteins or lipids, inexpensive, stably available at low cost, and free of unnecessary materials that are obstacles in the purification of a recombinant protein.

DETAILED DESCRIPTION OF THE INVENTION

Figure 1:
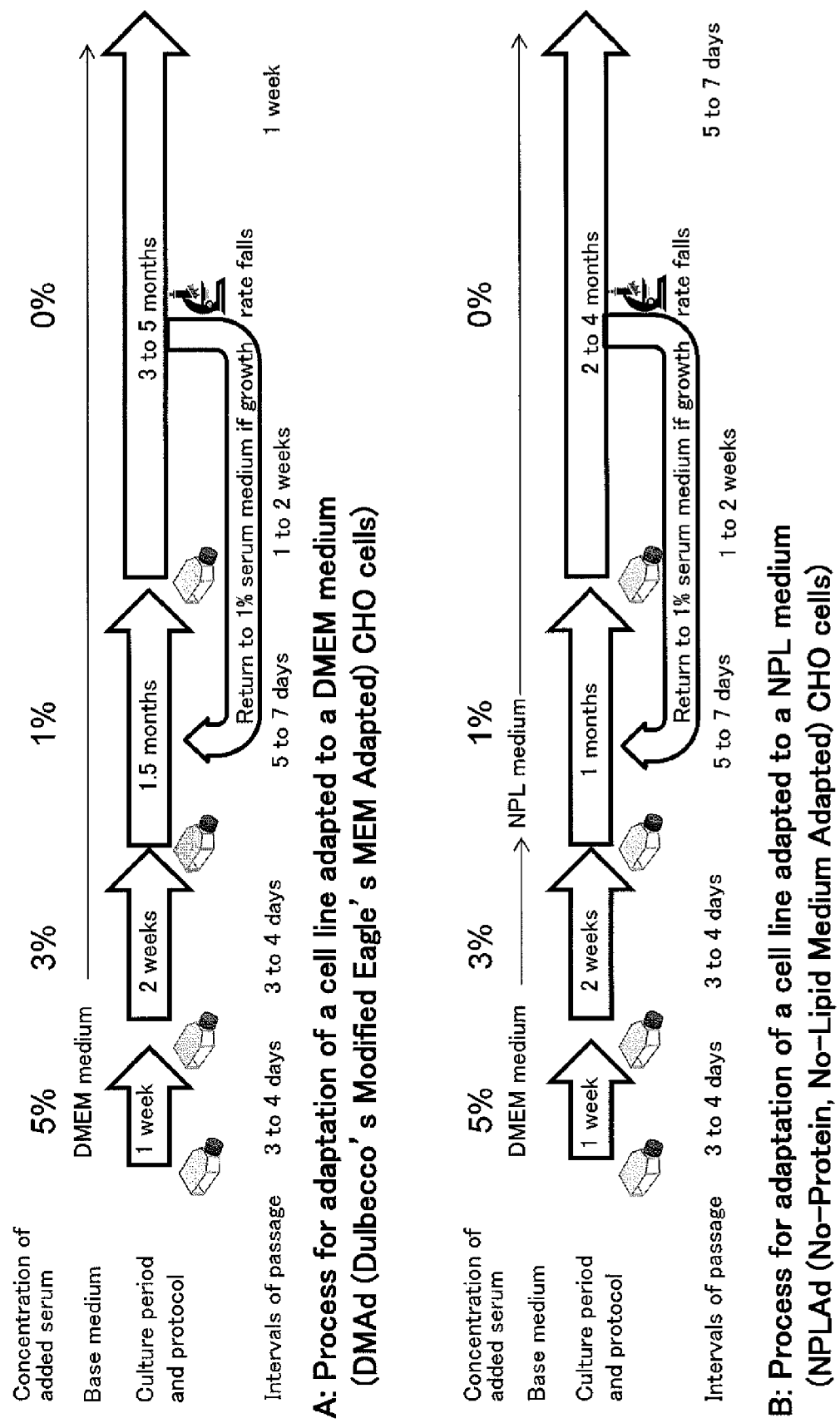
FIG. 1 is a diagram illustrating a protocol of the method for preparing the adapted cell line of the present invention. Panels A and B show methods for preparing a cell line adapted to a DMEM medium and another cell line adapted to an NPL medium, respectively.

As used in the present description and claims, the following terms have meanings as respectively defined below. An "established cell line" is defined as a cell line that has been confirmed to present no change in the growth rate or cellular morphology for three or more passages when the cells are plated at the same cell density upon passage. A "protein-free and lipid-free medium" means a medium that is substantially free of proteins or lipids, namely, a medium to which composition one or both of a protein and a lipid, or an additive comprising one or both of them (for example, a serum or a tissue extract) is not intentionally added. In this case, it may be allowed the presence of a small amount of a protein or a lipid, which is introduced into the medium as an impurity or a contaminant of an added component. A "growth factor" means a cytokine having a molecular weight of more than 810, which promotes proliferation of a specified cell. Examples of the growth factors include epidermal growth factor (EGF), insulin like growth factor (IGF), transforming growth factor (TGF), nerve growth factor (NGF), brain-derived neurotrophic factor (BDNF), vesicular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), basic fibroblast growth factor (bFGF, or FGF2), and hepatocyte growth factor (HGF).

The "DMEM medium (Dulbecco's modified Eagle's medium)" is a synthetic medium for mammal cells having a composition that has been obtained by Dulbecco (Dulbecco, Virology 1959 July; 8(3): 396-7) by modifying the Eagle's minimum essential medium (Eagle, Science 1959 Aug. 21; 130(3373): 432-7). The DMEM medium may contain components such as HEPES, phenol red, pyruvic acid and the like in varied amounts, as long as it is based on the Dulbecco's composition. However, DMEM media, to which a protein or a lipid has been added, are not included within the scope of the present invention.

1. A Protein-Free and Lipid-Free Medium

The protein-free and lipid-free medium according to the present invention has been obtained by modifying the DMEM medium. The original CHO cells have been continuously cultured for a long period of time in DMEM medium supplemented with serum. Therefore, the original CHO cells have been adapted to the composition of the DMEM medium. Thus, the DMEM medium was selected as the base medium in expectation that the CHO cells would readily be adapted to a modified DMEM medium.

The protein-free and lipid-free medium (hereafter, this may be called as an NPL medium) of the present invention was designed by using the DMEM medium as a base in order to improve the proliferation and the like of the cells. Decreased nutrient components caused by not adding a serum, especially decreased nonessential components, are compensated by syntheses of them through metabolism. However, the cell growth rate may decrease because of, e.g., the time lag until the completion of the syntheses of those components. Therefore, the composition of the NPL medium has been formulated by adding to the DMEM composition the following components that are not contained in the DMEM medium:

(1) Nonessential Amino Acids 1 to 100 mg/L, preferably 1 to 50 mg/L, and most preferably 10 mg/L of alanine; 5 to 100 mg/L, preferably 20 to 80 mg/L, and most preferably 50 mg/L of asparagine; 5 to 100 mg/L, preferably 5 to 50 mg/L, and most preferably 25 mg/L of asparagine acid; 5 to 100 mg/L, preferably 5 to 50 mg/L, and most preferably 20 mg/L of cysteine; 1 to 250 mg/L, preferably 100 to 250 mg/L, and most preferably 200 mg/L of glutamic acid; 1 to 100 mg/L, preferably 40 to 100 mg/L, and most preferably 70 mg/L of phenylalanine; and 10 to 100 mg/L, preferably 50 to 100 mg/L, and most preferably 100 mg/L of proline;

(2) Inorganic Salts 0.1 to 10 mg/L, preferably 0.5 to 5 mg/L, and most preferably 2 mg/L of zinc sulfate heptahydrate; 0.001 to 0.01 mg/L, preferably 0.001 to 0.008 mg/L, and most preferably 0.004 mg/L of sodium selenite; and 0.0001 to 0.005 mg/L, preferably 0.0001 to 0.003 mg/L, and most preferably 0.002 mg/L of copper (II) sulfate pentahydrate;

(3) Vitamins 0.001 to 1 mg/L, preferably 0.005 to 0.5 mg/L, and most preferably 0.01 mg/L of biotin; and 0.01 to 2 mg/L, preferably 0.01 to 1 mg/L, and most preferably 0.1 mg/L of vitamin B12;

(4) Precursors of Nucleic Acids 0.01 to 1 mg/L, preferably 0.05 to 0.8 mg/L, and most preferably 0.7 mg/L of thymidine; and 0.1 to 10 mg/L, preferably 0.5 to 7 mg/L, and most preferably 4 mg/L of hypoxanthine;

(5) Others 0.0001 to 2 mg/L, preferably 0.001 to 1 mg/L, and most preferably 0.2 mg/L of putrescine; and 0.1 to 5 mg/L, preferably 0.5 to 3 mg/L, and most preferably 1.5 mg/L of monoethanolamine.

Further, the amount of glucose is increased to 2000 to 5000 mg/L, i.e., 2 to 5 times of the usual amount in the DMEM medium.

To the NPL medium a low-molecular compound may be added as long as it is not a protein or a lipid. The medium is adjusted so that the final osmic pressure during use comes to be within the range of 200 to 400 mOsml/kg, preferably 250 to 350 mOsml/kg.

Further, to the NFL medium according to the present invention, 1 to 20 mg/L (preferably 1 to 15 mg/L) of insulin and/or 0.1 to 10 mg/L (preferably 1 to 5 mg/L) of ganglioside GM3 (1-O-[4-O-(3-O-α-neuraminosyl-β-D-galactopyranosyl)-β-D-gluco pyranosyl]ceramide) (Chemical Formula 1):

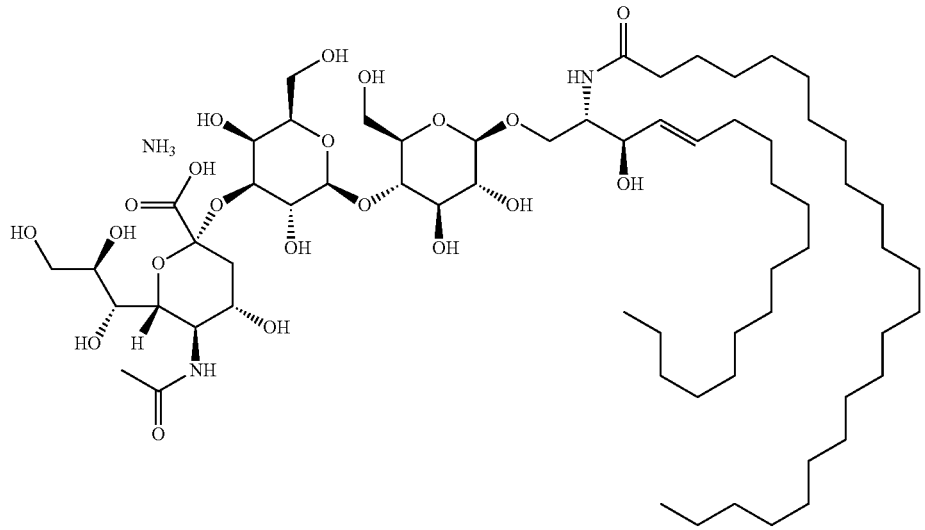

Chemical formula 1

By adding one or both of them, the growth rate of the cells is increased, or the term for adaptation can be shortened.

The NPL medium according to the present invention can be prepared as a dry composition or a concentrate comprising a part or entire set of the above constituents. By dissolving the dry composition or by diluting the concentrate before use, an aqueous solution comprising a composition of the NPL medium according to the present invention can be obtained. By using the dry composition or the concentrate, the NPL medium according to the present invention can be readily prepared just before its use.

2. A Method for Establishing an Adapted CHO Cell Line

As the original CHO cells, commercially available cells can be used. CHO cells that have been usually maintained in a medium supplemented with serum are passaged while gradually decreasing the serum concentration, and are adapted until they finally come to stably proliferate in a serum- and growth factor-free medium. As the medium that is used in the adaptation process, a standard medium such as the DMEM medium can be used. However, to attain a stable proliferation property in a serum-free medium, it is preferable to use the NPL medium according to the present invention. Further, an NPL medium supplemented with insulin and/or GM3 is preferred because the cells can be adapted in a shorter period of time by using the medium.

The adapted cell line thus established has acquired such ability that the cells stably proliferate in a suspended state in a static culture. Therefore, the cells of the adapted cell line of the present invention can be readily cultured in a suspended state in large quantity in a spinner or a tank without using a carrier or an agent for suspension.

The adapted CHO cell line that had been established by using the NPL medium was deposited in the National Institute of Technology and Evaluation Patent Microorganisms Depository (NPMD), Kamatari 2-5-8, Kazusa, Kisarazu, Chiba, Japan, on Jun. 28, 2013, as Identification reference "NPLAd001," and Accession number of NITE BP-01641 was assigned.

3. A Process for Producing a Recombinant Protein

The cell line adapted to a protein-free and lipid-free medium according to the present invention can be used for the production of a recombinant protein by transfecting the cell with a gene that encodes a desirable protein. The method for producing a vector that carries the gene to be transfected and the method for transfection are not specifically restricted as long as those methods can be applied for the CHO cells. Methods that are used in this technical field can be used. The cells of the cell line adapted to a protein-free and lipid-free medium according to the present invention can be cultured in a suspended state in large quantity. Further, the cells of the present invention have a protein-productivity that is several times higher than that of the original CHO cells. Therefore, when the cells of the present invention are used, sufficient yields can be secured even by the transient method. In the production of a recombinant protein, any protein-free and lipid-free media such as DMEM and NPL can be used. However, by culturing cells in a medium supplemented with GM3 and/or insulin before transfection and conducting the transfection in another medium comprising no GM3, the recombinant protein can be efficiently produced.

The protein to be produced by the method of the present invention is not particularly limited as long as it can be produced in CHO cells, and includes tissue plasminogen activator, enzymes (exemplary enzymes include glucocerebrosidase, alpha-L-iduronidse, acidic alpha-glucosidase, human N-acetyl galactosamine-4-sulfatases, urate oxidase, DNases, and the like), blood coagulation factor IX, thrombomodulin, follicle-stimulating hormone, interferons, erythropoietin, antibodies (as examples, anti-CD20 antibody, anti-IL6 receptor antibody, anti-VEGF antibody, TNF-alpha antibody, anti-IgE antibody, anti-RANKL antibody, anti-CCR4 antibody, and the like) and so on. The recombinant protein produced can be recovered and purified from the cells according to the present invention or the medium by using any methods that are used in this technical field depending on the feature of the protein.

EXAMPLES

1. Establishment of a CHO Cell Line Adapted to a Protein-Free and Lipid-Free Medium by a Method for Adaption to a Medium By using a method for adaption to a medium, two types of CHO cell lines were established as follows.

(1) Cells

The original CHO-K1 cells that were used in the method for adaption to a medium were purchased from the European Collection of Cell Cultures (ECACC). These cells were maintained in a Dulbecco's Modified Eagle's MEM (DMEM) medium (Kyokuto Pharmaceutical Industry) supplemented with 10% fetal bovine serum (FBS).

(2) Media

To apply the method for adaption to a medium to the original CHO cells, the DMEM medium (Kyokuto Pharmaceutical Industry) and an NPL medium, which are shown in Table 1, were used.

Each medium was prepared by dissolving prescribed constituents in distilled water to obtain the predetermined final concentrations of the constituents, followed by sterilization by filtration.

TABLE 1

(Unit: mg/L)

| INGREDIENTS | DMEM | NPL | INGREDIENTS | DMEM | NPL |
|---|---|---|---|---|---|
| NaCl | 6,400 | 6,400 | L-Leucine | 105 | 105 |
| KCl | 400 | 400 | L-Lysine•HCl | 146 | 146 |
| CaCl$_2$ (anhyd.) | 200 | 200 | L-Methionine | 30 | 30 |
| MgSO$_4$ (anhyd.) | 98 | 98 | L-Phenylalanine | | 66 |
| NaH$_2$PO$_4$ (anhyd.) | 109 | 109 | L-Proline | | 100 |
| Fe(NO$_3$)$_3$•9H$_2$O | 0.1 | 0.2 | L-Serine | 42 | 42 |
| ZnSO$_4$•7H$_2$O | | 2.0 | L-Threonine | 95 | 95 |
| Na$_2$SeO$_3$ | | 0.0043 | L-Tryptophan | 16 | 16 |
| CuSO$_4$•5H$_2$O | | 0.002 | L-Tyrosine•HCl | 72 | 72 |
| HEPES | | 4,000 | L-Valine | 94 | 94 |
| Glucose (anhyd.) | 1,000 | 4,000 | Biotin | | 0.01 |
| Sodium Pyruvate | 110 | 110 | D-Ca Pantothenate | 4.0 | 4.0 |
| Phenol Red | 15 | 15 | Choline Chloride | 4.0 | 4.0 |
| L-Alanine | | 10 | Vitamin B12 | | 0.1 |
| L-Arginine•HCl | 84 | 164 | Folic Acid | 4.0 | 4.0 |
| L-Aspragine•H$_2$O | | 50 | myo-Inositol | 7.2 | 7.2 |
| L-Aspartic Acid | | 25 | Niacineamide | 4.0 | 4.0 |
| L-Cystein HCl•H$_2$O | | 20 | Pyridoxal HCl | 4.0 | 4.0 |
| L-Cystine•2HCl | 63 | 63 | Riboflavin | 0.4 | 0.4 |
| L-Glutamic Acid | | 200 | Thiamine HCl | 4.0 | 4.0 |
| L-Glutamine | 584 | 584 | Putrescine 2HCl | | 0.2 |
| Glycine | 30 | 30 | Thymidine | | 0.7 |
| L-Histidine HCl•H$_2$O | 42 | 42 | Hypoxanthine Na | | 4.0 |
| L-Isoleucine | 105 | 105 | Monoethanolamine | | 1.53 |

(3) a Method for Adaption to a Medium (3-1) Adaptation by Using a DMEM Medium

The adaptation by using a DMEM medium was carried out according to the following procedure (FIG. 1, Panel A). First, starting from the DMEM medium supplemented with 10% FBS, i.e., the medium that was used for maintaining the cells of the original CHO cell line, the cells were incubated for about one week while sequentially lowering the serum concentration to 3%. Further, incubation of the cells was continued in a DMEM medium supplemented with 1% FBS for one month. Until the cell proliferation property became stable, the cells were incubated in a DMEM medium supplemented with 1% FBS medium. When the cell proliferation property became stable, the supplementation of the serum was stopped. The incubation of the cells was continued thereafter.

When the cell growth rate markedly lowered by culturing in a serum-free DMEM medium, the cells were returned to a medium comprising 1% of a serum, and cultured until the proliferation property was restored. When the proliferation property became stable, culturing of the cells in a serum-free medium was resumed. These operations were repeated until the cells were able to be stably cultured in the serum-free medium. The culture was carried out under conditions of 37 degrees Celsius and 5% $CO_2$.

The cell line that had been adapted to the serum-free medium by using a DMEM medium was named as "DMAd CHO cells." For the following experimentations, DMAd CHO cells that had experienced at least thirty passages after adaptation were used.

The definition of the adapted cell line is as follows: When the growth rate becomes stable, cells having a viability of at least 90% are seeded in a culture flask (25 $cm^2$-size) at a cell density of 100,000 cells/mL, and then continuously cultured. When the growth rate and the cell morphologies are not altered for at least three passages, the cells are established as an adapted cell line.

(3-2) Adaptation by Using an NPL Medium

The adaptation by using an NPL medium was carried out according to the following procedure (FIG. 1, Panel B). First, starting from the DMEM medium supplemented with 10% FBS, i.e., the medium that was used for maintaining the cells of the original CHO cell line, the cells were incubated for about one week while sequentially lowering the serum concentration to 3%. Further, incubation of the cells was continued in an NPL medium supplemented with 1% FBS for two weeks. Until the cell proliferation property became stable, the cells were incubated in an NPL medium supplemented with 1% FBS medium. When the cell proliferation property became stable, the supplementation of the serum was stopped. The incubation of the cells was continued thereafter.

When the cell growth rate markedly lowered by culturing in a serum-free NPL medium, the cells were returned to a medium comprising 1% of a serum, and incubated until the proliferation property was restored. When the proliferation property became stable, culturing of the cells in a serum-free medium was resumed. These operations were repeated until the cells were able to be stably cultured in the serum-free medium. The culture was carried out under conditions of 37 degrees Celsius and 5% $CO_2$. The cell line that had been adapted to the serum-free medium by using an NFL medium was named as "NPLAd CHO cells." For the following experimentations, NPLAd CHO cells that had experienced at least two-hundred passages after adaptation were used.

(4) Results

Figure 2:
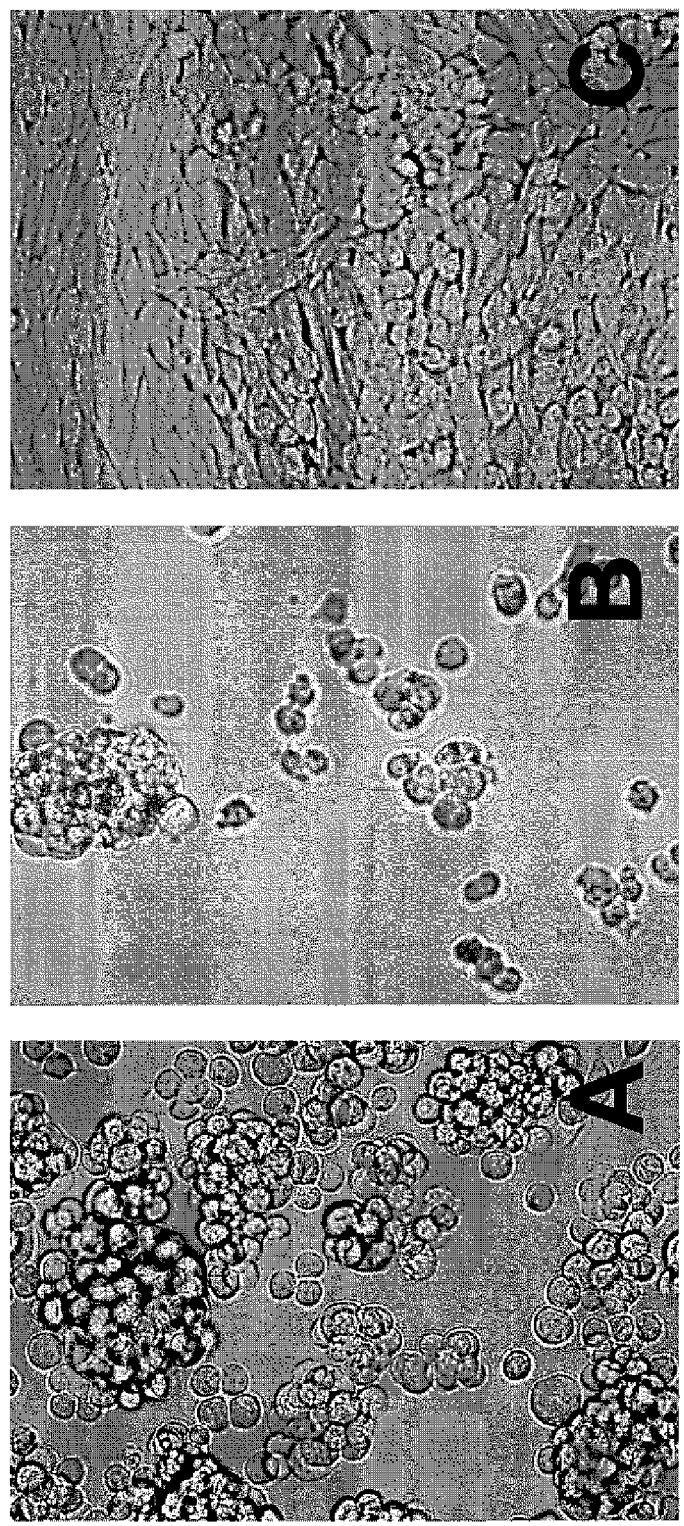
FIG. 2 is an inverted phase-contrast microphotograph (100 magnifications) that shows cellular morphology of the cells adapted to a protein-free and lipid-free medium according to the present invention. Panel A: NPLAd CHO cells; Panel B: DMAd CHO cells; and Panel C: Original CHO-K1 cell line.

In the two cases in which the DMEM medium and the NPL medium were respectively used, adapted cell lines were able to be established. The morphologies of the cells of the established adapted cell lines and the cells of the original cell line are shown in FIG. 2. During their subcultures, the NPLAd CHO cells (Panel A), the DMAd CHO cells (Panel B), and the cells of the original CHO-K1 cell line were observed by using an inverted phase-contrast microscope (100 magnifications). The CHO cells of the original cell line showed cobblestone-like proliferation (Panel C). In contrast, the DMAd CHO cells (Panel B) and the NPLAd CHO cells (Panel A), which had been adapted to a protein-free and lipid-free medium, were in a suspended state as single cells or aggregates. Usually, to suspend the CHO cells, shaking or addition of a flotation agent such as a surfactant is required. However, without these operations, the cells of the adapted cell lines were able to be suspension-cultured as aggregates.

It has been said that the CHO cells require lipids and growth factors, which are supplied from a serum, for proliferation. It is thought that the adapted cells came to be able to produce these substances by themselves during the adaptation process. Further, in contrast to the CHO cells of the original cell line, the two adapted cell lines were both acquired altered phenotypes that allow the cells to be suspension-cultured as aggregates without any treatment for realizing the suspended state. Namely, the cells came to be able to proliferate in a suspended state without a flotation agent or the like.

The growth rates of the adapted cell lines according to the present invention were slightly inferior to that of the original CHO cell line when cells were in static cultures using culture flasks as described above. The DMAd CHO cells reached confluency in one week to ten days. In contrast, the NPLAd CHO cells reached confluency five days after the start of the culture and required to be subcultured. Thus, the growth rate of the NPLAd CHO cells was faster than that of the DMAd CHO cells. The interval between subcultures is 3 to 4 days for the original CHO cells. Thus, the growth rates of the NPLAd CHO cell line and the DMAd CHO cell line were slightly slower as compared to that of the original cell line.

The cell lines adapted to a protein-free and lipid-free medium depend on only autologous growth factors for cell proliferation. Thus, the slower growth rates may be attributable to several causes such as deficiency of factors other than autologous growth factors and functional deterioration of the cells because of deficiency of proteins and/or lipids for a long period of time. However, it is accepted that the use of a spinner or a culturing apparatus of a bioreactor-type allows efficient exchange of nutrient components and oxygen supply, and thus allows cultures at a more rapid growth rate and at a higher cell density, as compared to the static culture. Thus, it is likely that such a difference of the cell growth rates of this level can be adequately compensated by the selection or improvement of the culturing method.

The adapted NPLAd CHO cell line that had been established was deposited in the National Institute of Technology and Evaluation Patent Microorganisms Depository (NPMD), Kamatari 2-5-8, Kazusa, Kisarazu, Chiba, Japan, on Jun. 28, 2013, as Identification reference of "NPLAd001," and Accession number of NITE P-01641 was assigned 2. Study of Adherence Property of the CHO Cells Adapted to a Protein-Free and Lipid-Free Medium Adherent cells, which are usually cultured by using a serum, adhere to a wall of a culture vessel by binding a cell-adhesion factor such as integrin, which is secreted by the cells themselves, through an ECM contained in the serum, such as fibronectin. The reason that the adapted cells can be cultured in a suspended state, unlike its original cells that are cultured in an adhesion state, may be because an ECM is not supplied from the protein-free and lipid-free medium. Therefore, whether the NPLAd CHO cells become adherent was studied by seeding and culturing the NPLAd CHO cells using plates, which had been coated with an ECM (such as fibronectin or type-I collagen) or albumin.

(1) Culture Substrate

The following culture substrates were used: (1) a fibronectin-coated 24-well plate (manufactured by Japan Becton, Dickinson and Company; "Fibronectin-coated 24-well plate"), (2) a type I collagen-coated 24-well plate (manufactured by Japan Becton, Dickinson and Company; "Type I collagen-coated 24-well plate"), (3) an albumin-coated 24-well plate (produced by dispensing 1 mL of phosphate buffered saline (PBS) comprising 1 mg/mL of bovine serum albumin (BSA) into the 24-well plate manufactured by Japan Becton, Dickinson and Company, incubating the plate at 37 degrees Celsius for 2 hours, rinsing with PBS twice so as to wash extra BSA off, and drying it under sterile conditions in a clean bench), and (4) an untreated plate (a 24-well plate manufactured by Japan Becton, Dickinson and Company).

(2) Experimental Method

The NPLAd CHO cells were used as the cells and the NPL medium was used as the medium. The NPLAd CHO cells, which had been maintained in the NPL medium, were washed twice with the NPL medium. After washing, the cell aggregates were suspended in the NPL medium and the number of the cells was counted by a dye-exclusion test by using the improved Neubauer hemocytometer and trypan blue, and a viability was calculated. After it was confirmed that the viability was 90% or more, the cell number was adjusted to 50,000 cells/mL with the NPL medium. The cells were seeded in wells of the fibronectin-coated 24-well plate, the type I collagen-coated 24-well plate, the albumin-coated 24-well plate, and the untreated 24 well plate in an amount of 1 mL/well.

The plates, where the cells had been seeded, were incubated for five days under conditions of 37 degrees Celsius and 5% $CO_2$. Then, it was observed by using an inverted phase-contrast microscope (40 magnifications) whether the cells adhered during culture.

(3) Results

Figure 3:
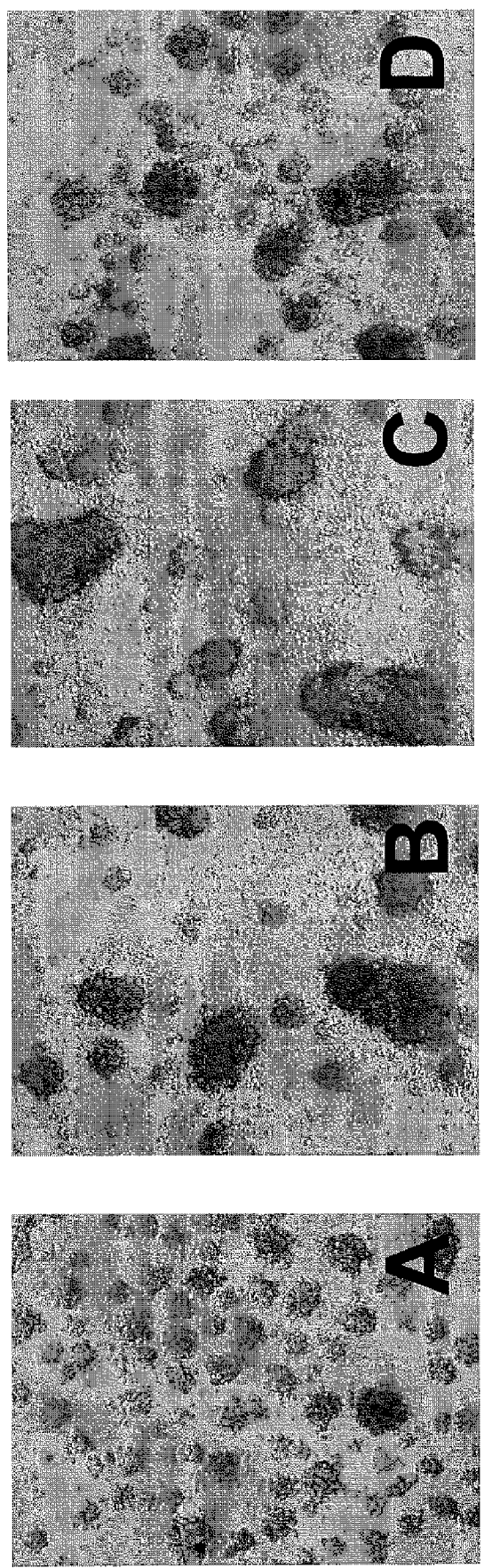
FIG. 3 is an inverted phase-contrast microphotograph (40 magnifications) which shows influences of ECMs to the cellular morphology of the cells adapted to a protein-free and lipid-free medium according to the present invention (NPLAd CHO cells). Panel A: No treatment plate; Panel B: fibronectin-coated plate; Panel C: Type 1 collagen-coated plate; and Panel D: albumin-coated plate.

FIG. 3 shows the cell morphologies on the respective plates five days after the start of the culture. The cells on the fibronectin-coated plate (Panel B), the type I collagen-coated plate (Panel C), and the albumin-coated plate (Panel D) were in the forms of aggregates, and suspended without adhesion, as the cells on the untreated plate. Among these cells, there was no difference. The possibility cannot be denied that the cells adhered once to a culture substrate and then detached from the culture substrate after the cells reached confluency. Therefore, the cells were continuously observed. As a result, it was observed that the NPLAd CHO cells proliferated without adhering to the culture substrate from the beginning of the culture. From the above results, it was understood that the reason why the cells of the adapted cell line were able to be suspended was not due to the deficiency of ECMs.

In the case where the disappearance of the adhesion property is not due to the deficiency of ECMs, another possibility is that a cell-adhesion factor such as integrin is not sufficiently generated. Further, alteration of the cell membrane structure can also be possible. The lipids including phospholipids are, in addition to those biosynthesized from sugars, incorporated into the cells through albumin that is a carrier protein in blood, and are used in, e.g., the cell membrane. In the case of the adapted cell line, there is a possibility that the structure of the cell membrane has been altered due to the deficiency of the lipids for a long period of time, which in turn has affected the adhesion property of the cells.

3. Verification of Reversibility of Phenotypic Alteration of the CHO Cells Adapted to a Protein-Free and Lipid-Free Medium The CHO cells of the original cell line cannot proliferate in a protein-free and lipid-free medium. However, the cells of the adapted cell lines can proliferate under an oligotrophic condition because they have adapted to the protein-free and lipid-free medium. There is a possibility that this phenotypic change has resulted from a clone cell that had come to be able to proliferate under an oligotrophic condition by a genetic mutation and became dominant during the culture. In the case where the phenotypic change of the CHO cells is due to a genetic mutation, there is a possibility that an unpredictable transformation may have also been occurred due to, e.g., a genetic point mutation, a genetic deletion by a partial chromosome elimination, or a deletion of chromosome, thereby the cellular function per se may have been damaged. Such damaged cells are not ensured in terms of their stabilities as cells used in production systems. Further, similar properties may not necessarily be obtained even if the same procedure is used. Thus, the reproducibility of the medium adaptation method may not be ensured as well. Therefore, to investigate whether the phenotypic change of the adapted cell line is associated with a genetic mutation, reversibility of this phenotypic change was studied. Namely, the cells of the adapted cell line were returned in a medium supplemented with a serum, and whether the cells showed cell morphologies and growth rates similar to those of the CHO cells of the original cell line was examined.

(1) Experimental Method (1-1) Reverse Adaptation Cultures of the DMAd CHO Cells and the NPLAd CHO Cells.

The DMAd CHO cells that had been continuously cultured for at least thirty passages after establishment and the NPLAd CHO cells that had been continuously cultured for at least two hundreds and eighty passages after establishment were used as the cells. The DMEM medium supplemented with 10% FBS was used as the medium.

The DMAd CHO cells and the NPLAd CHO cells were respectively washed twice with a DMEM medium, and then respectively suspended in the DMEM medium by dispersing cells of aggregates. Thereafter, the numbers of the cells were respectively counted by a dye-exclusion test by using the improved Neubauer hemocytometer and trypan blue, and viabilities were respectively calculated. By diluting with the DMEM medium supplemented with 10% FBS, the cell number was adjusted to 100,000 cells/mL. The diluted cell suspension, 5 mL, was poured into a culture flask of 25 $cm^2$, and the cells were cultured under conditions of 37 degrees Celsius and 5% $CO_2$. When the cells reached confluency, the cells were subcultured by the same procedures.

In the case where the cells adhered to the wall of the flask, after recovering suspended cells, the adhered cells were detached and dispersed by using trypsin. Not to select cells having properties of a specific tendency, when the cells were again seeded, a mixture of floating cells and adhered cells was used. The DMAd CHO cells and the NPLAd CHO cells, which had been reversely adapted, were respectively named as the reverse-adapted DMAd CHO cells and the reverse-adapted NPLA d CHO cells.

(1-2) Determination of Growth Rate of the Reverse-Adapted Cell Line

The CHO cells of the original cell line, the DMAd CHO cells, and the reverse-adapted DMAd CHO cells, which had been continuously cultured for at least twenty-five passaged in the reverse adaptation medium, were used. As the media, the DMEM medium supplemented with 10% FBS was used for the CHO cells of the original cell line and the reverse-adapted DMAd CHO cells, and the DMEM was used for the DMAd CHO cells.

Because the CHO cells of the original cell line and the reverse-adapted DMAd CHO cells adhered to the wall of the flask, they were detached and dispersed by using trypsin. Then, the numbers of the cells were respectively counted by a dye-exclusion test by using the improved Neubauer hemocytometer and trypan blue, and the viabilities were respectively calculated. The DMAd CHO cells were suspended in the DMEM medium to disperse the cells of aggregates. Thereafter, the number of the cells was counted by a dye-exclusion test by using the improved Neubauer hemocytometer and trypan blue, and the viability was calculated.

The CHO cells of the original cell line, the DMAd CHO cells, and the reverse-adapted DMAd CHO cells were respectively diluted with the respective passage media to 50,000 cells/mL. The cells were respectively seeded in wells of 24-well plates at 1 mL/well. The plates after seeding were incubated for seven days under conditions of 37 degrees Celsius and 5% $CO_2$. At regular time intervals, the cell numbers were respectively counted by a dye-exclusion test by using the improved Neubauer hemocytometer and trypan blue, and the viabilities were respectively calculated. The NPLAd cells and the reverse-adapted NPLAd CHO cells were respectively cultured and their viabilities were calculated in the same manner.

(2) Results

Figure 4:
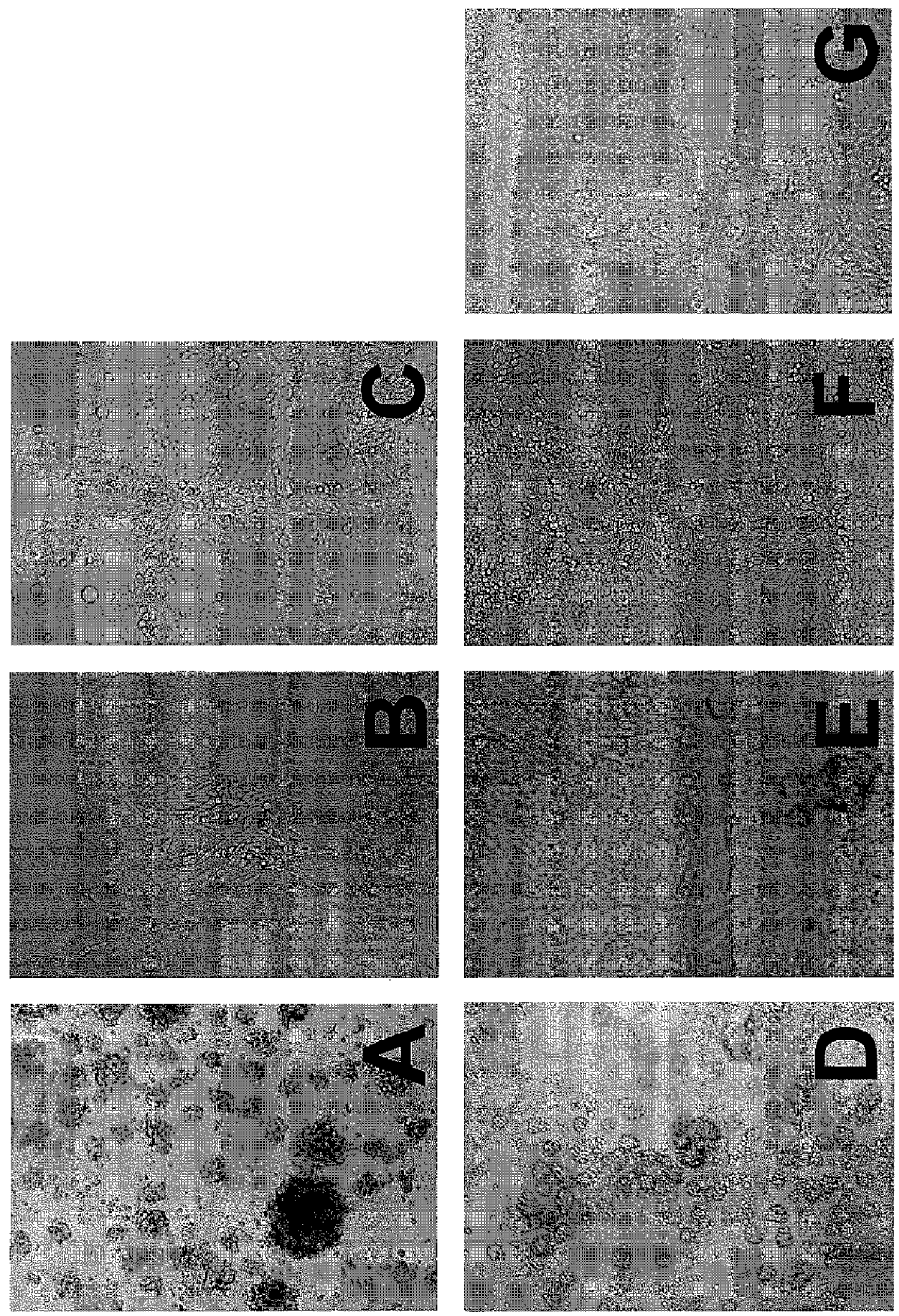
FIG. 4 is an inverted phase-contrast microphotograph (40 magnifications) which shows influences of the addition of a serum to the cellular morphology of the cells adapted to a protein-free and lipid-free medium according to the present invention. Panel A: DMAd CHO cells; Panel B: Reverse-adapted DMAd CHO cells (the third passage); Panel C: Reverse-adapted DMAd CHO cells (the twentieth passage); Panel D: NPLAd CHO cells; Panel E: Reverse-adapted NPLAd CHO cells (the second passage); Panel F: Reverse-adapted NPLAd CHO cells (the ninth passage); and Panel G: Original CHO cells.

FIG. 4 shows the cell morphologies of the CHO cells of the original cell line, the DMAd CHO cells, the NPLAd cells, the reverse-adapted DMAd CHO cells and the reverse-adapted NPLAd CHO cells, which had been cultured for reverse adaptation to the DMEM medium supplemented with a serum. The alterations of the cell morphologies were observed with the inverted phase-contrast microscope (40 magnifications). In the reverse adaptation cultures, parts of the DMAd CHO cells and the NPLAd CHO cells adhered just after the start of the culture with a serum. By continuing subculture, the DMAd CHO cells and the NPLAd CHO cells shifted to adhesive morphologies. In the reverse-adapted DMAd CHO cells of the third passage (Panel B) and the reverse-adapted NPLAd CHO cells of the second passage (Panel E), adhered cells and suspended cells having spherical shapes were observed in a mixed state. No differences in morphologies were observed between the reverse-adapted DMAd CHO cells of the twentieth passage (Panel C) and the CHO cells of the original cell line (Panel G), and between the reverse-adapted NPLAd CHO cells of the ninth passage (Panel F) and the CHO cells of the original cell line (Panel G).

Figure 5:
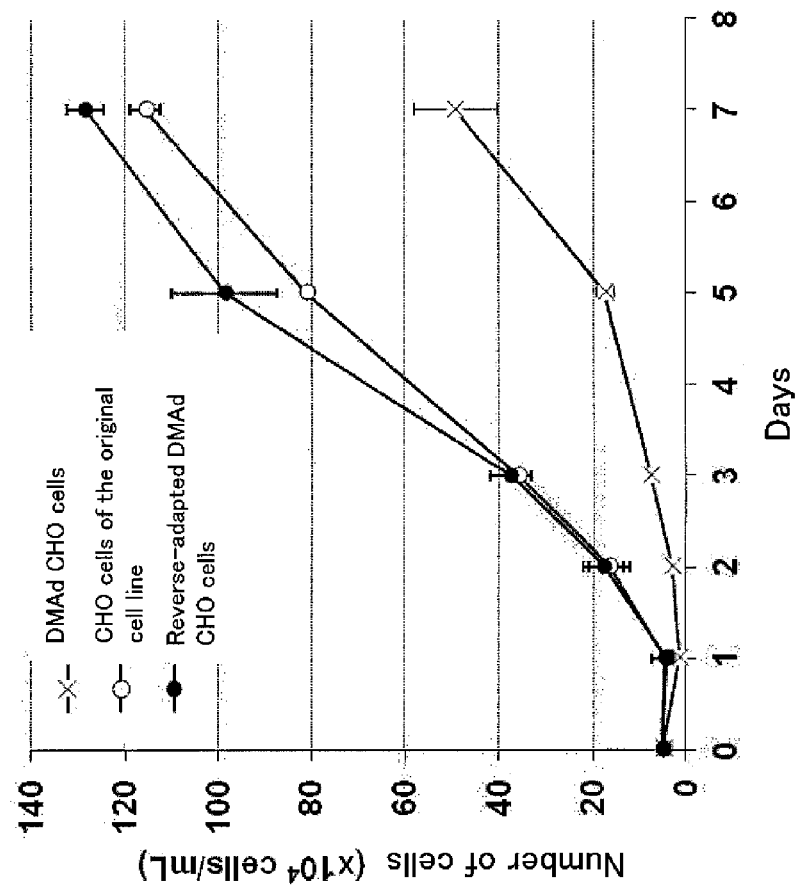
FIG. 5 is a figure that shows reversion of the cell growth rates by a reverse-adapting culture method. -○-: Original CHO cells; -X-: DMAd CHO cells; and -●-: Reverse-adapted DMAd CHO cells (the twenty-fifth passage). The numerical values are shown as an average (of three wells for each group) ±SD.

FIG. 5 shows the growth rates of respective cell lines. The cell growth rates of the reverse-adapted DMAd CHO cells (-●-) and the CHO cells of the original cell line (-○-) were higher than that of the DMAd CHO cells (-X-), and were almost the same. The reverse-adapted DMAd CHO cells and the CHO cells of the original cell line had the same cell growth rates up to the third day of culture. At the seventh day, the growth rate of the reverse-adapted DMAd CHO cells was slightly higher, but there was no significant difference, Similar results were obtained for the NPLAd CHO cells (the data were not shown).

The phenotypic change of the CHO cell line adapted to a protein-free and lipid-free medium, which had been established, was reversible, and it was possible to reverse the cell morphology and the proliferation property to those that are similar to the CHO cells of the original cell line by culturing in the presence of a serum. The DMAd CHO cells used and the NPLAd CHO cells used were, after their establishments, more than thirty passages and more than two hundreds and eighty passages, respectively. By this experiment, it was confirmed that their phenotypic changes were not fixed even though the cells were continuously cultured for a long period of time. Further, it was confirmed that the morphology of the NPLAd CHO cells, which had been continuously cultured for more than four hundred passages, was restored to that of the original cell line by the reverse adaptation with the addition of a serum (the data were not shown). From these results, it is thought that the phenotypic change of the CHO cell line adapted to a protein-free and lipid-free medium, which was established, is not an irreversible change associated with a genetic mutation.

It is thought that a cell line having properties similar to those of the cell lines of the present invention can be reproducibly established by the method of the present invention, because the adapted cell lines of the present invention involve no genetic mutation and the possibility that the properties were incidentally obtained was low. Thus, the present invention has realized desirable phenotypes important for the safety and productivity in biopharmaceutical productions without an unpredictable a phenotypic change due to mutation. Therefore, the adapted cells and the method for preparing them of the present invention are useful as a cell line for the stable production of biopharmaceuticals and as a method for preparing the cell line, respectively.

4. Reactivity of the CHO Cells Adapted to a Protein-Free and Lipid-Free Medium to Cell Growth Factors For cell lines that are used for industrial application, high proliferation ability and high productivity of a substance are required. To enhance the growth rate of the adapted cell line of the present invention, responsiveness of the cells to cell growth factors were studied.

It is said that usually the CHO cells proliferate depending on growth factors that are supplied from a serum or biological materials in the medium. However, the protein-free and lipid-free medium, which was used for the culture for adaptation, does not comprise a serum or biological materials at all. Therefore, the growth factors are not supplied from the medium. Thus, it is thought that the cells of the adapted cell line produce growth factors in an autocrine-like manner to proliferate. There is a possibility that the membrane structure has been altered due to the deficient of the lipids for a long period of time, in which period of time the cells have been adapted to the protein-free and lipid-free medium. Therefore, it is thought that there is a possibility that the proliferation ability of the adapted cell line can be improved by increasing the expression of growth factors by the cells, or by normalizing the membrane structure so that signals of the growth factors can be fully received.

First, to study the involvement of an autocrine factor in the adapted cell line, a blocking test of a growth factor to its receptor was carried out by using a neutralizing antibody. As an autocrine factor of the adapted cell line, EGF was noticed. This is because there is a report (Fisher, et. al., Mead Johnson Symp Perinat Dev Med., 1988, 33-40) that EGF works as a growth factor in many types of epidermal or epithelial cells including CHO cells. Therefore, it was examined whether the proliferation was controlled by inhibiting the binding between EGF and the receptor by an anti-EGF neutralizing antibody. If the proliferation is inhibited by the anti-EGF neutralizing antibody, it can be judged that as an autocrine factor EGF is responsible for the proliferation of the adapted cell line.

Next, the addition of an endcrine factor was contemplated to induce further proliferation of the cells of the adapted cell line. As the endcrine factor, insulin was noticed. Insulin is a typical endcrine factor that is produced by the β-cells of the pancreatic islet of Langerhans, is an essential growth factor for many cells, and is reported to contribute to the proliferation of the CHO cells (Chun, et. al., Biotechnol Frog., 2003, 19, 52-7).

The insulin is a growth factor and was also commercialized in 1922 as a therapeutic medicine for diabetes (Rosenfeld, Clin Chem., 2002, 2270-88). It is one of the oldest recombinant pharmaceuticals. Its stability is higher than those of other proteinaceous growth factors, and it is inexpensive as compared to other recombinant growth factors because it is produced in a large scale. Because of these reasons, insulin was used in this study.

(1) Effect of Anti-EGF Antibody Against Proliferation of NPLAd CHO Cells and Induction of Cell Proliferation by Insulin Commercially available anti-EGF antibody (by R & D Systems, Inc.) and commercially available recombinant insulin (by Sigma-Aldrich) were used.

The NPLAd CHO cells were used as the cells and the NPL medium was used as the medium. The NPLAd CHO cells that had been maintained in the NPL medium were washed twice with the NPL medium. After washing, the cell of aggregates were suspended and dispersed in the NPL medium. Thereafter, the number of the cells was counted by a dye-exclusion test by using the improved Neubauer hemocytometer and trypan blue, and the viability was calculated. After it was confirmed that the viability was 90% or more, the cell number was adjusted to 50,000 cells/mL in the NPL medium. The cells were seeded in wells of the 24-well plate at 1 mL/well. To a half of the wells, in which the cells had been seeded, the anti-EGF neutralizing antibody was added so as to be a concentration of 5 mg/mL.

To the wells containing seeded cells, to which the anti-EGF neutralizing antibody had or had not been added, insulin was added so as to be the concentrations of 0, 1, 2, 5, or 10 mg/L. The plates, where the cells had been seeded, were incubated for five days under conditions of 37 degrees Celsius and 5% $CO_2$. Then, the numbers of the cells were respectively counted by a dye-exclusion test by using the improved Neubauer hemocytometer and trypan blue, and the viabilities were respectively calculated.

(2) Comparison of the Proliferation of the Insulin-Added NPLAd CHO Cells to that of the CHO Cells of the Original Cell Line The CHO cells of the original cell line and the NPLAd CHO cells were used. For the NPLAd CHO cells, an NPL medium supplemented with 10 mg/L of insulin (by Sigma-Aldrich) was used. For the CHO cells of the original cell line, a DMEM medium supplemented with 10% FBS was used.

Because the CHO cells of the original cell line were adherent cells, they were detached and dispersed by using trypsin. Thereafter, the number of the cells was counted by a dye-exclusion test by using the improved Neubauer hemocytometer and trypan blue, and the viability was calculated. As for the NPLAd CHO cells, the cells of aggregates were suspended and dispersed in the NPL medium. Thereafter, the number of the cells was counted by a dye-exclusion test by using the improved Neubauer hemocytometer and trypan blue, and the viability was calculated.

The CHO cells of the original cell line and the NPLAd CHO cells were diluted to a cell number of 50,000 cells/mL in the DMEM medium supplemented with 10% FBS and the NPL medium supplemented with insulin, respectively. The entire cells were seeded at 1 mL/well on 24-well plates. The plates, on which the cells had been seeded, were incubated for five days under conditions of 37 degrees Celsius and 5% $CO_2$. Then, the numbers of the cells were respectively counted by a dye-exclusion test by using the improved Neubauer hemocytometer and trypan blue, and the viabilities were respectively calculated. As the test to examine whether there was a significant difference, the Student's t-test was used.

(3) Results

Figure 6:
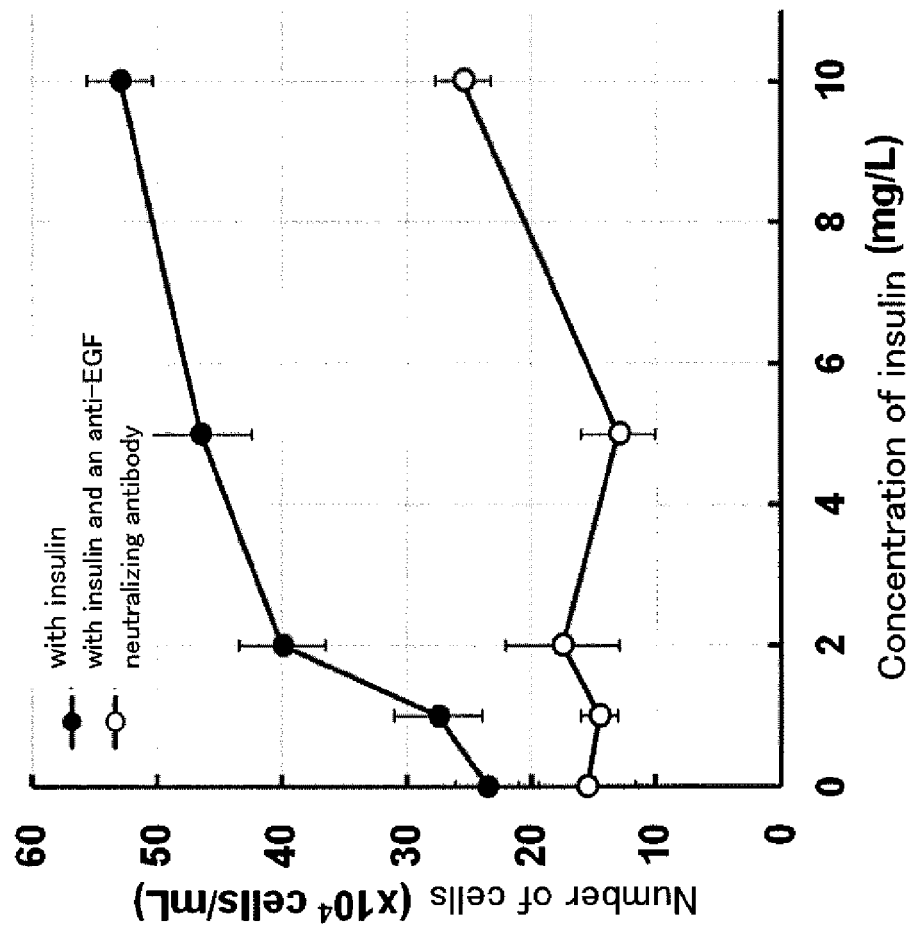
FIG. 6 is a figure that shows influences of an anti-EGF neutralizing antibody on the proliferation of the NPLAd CHO cells and the induction of cell proliferation by insulin. -●-: insulin was added; -○-: insulin and an anti-EGF neutralizing antibody (5 mg/mL) were added. The numerical values are shown as an average (of three wells for each group)±SD.

The effects of EGF, and insulin, which had been said to have an effect of proliferation induction to CHO cells, on proliferation of the adapted cells were studied. FIG. 6 shows an insulin concentration-dependent cell proliferation of the NPLAd CHO cells on the fifth day from the start of the culture.

In the case where the anti-EGF neutralizing antibody was added to the NPL medium (-○-), the proliferation of the NPLAd CHO cells was inhibited irrespective of the concentration of insulin added. Especially, in the case where insulin was not added and the anti-EGF neutralizing antibody was not added, the cell number (insulin concentration being 0 mg/L of -●-) was 235,000 cells/mL, whereas in the case where the insulin was not added and the anti-EGF neutralizing antibody was added, the cell number (insulin concentration being 0 mg/L of -○-) was 155,000 cells/mL. Namely, the proliferation was inhibited by about 35%. This result reveals that the proliferation of the NPLAd CHO cells depends on EGF, irrespective of the presence or absence of insulin. Further, because the NPL medium comprise no EGF, it was suggested that EGF, of which binding to the receptor had been inhibited by the anti-EGF neutralizing antibody, was produced by the NPLAd CHO cells per se, namely, it was an autocrine growth factor. However, even if the binding of EGF was inhibited by the anti-EGF neutralizing antibody, the cell number increased to about three-fold from the number of the cells seeded (50,000 cells/mL) on the fifth day of culture. Thus, it is thought that an autocrine factor or factors other than EGF are involved.

Figure 7:
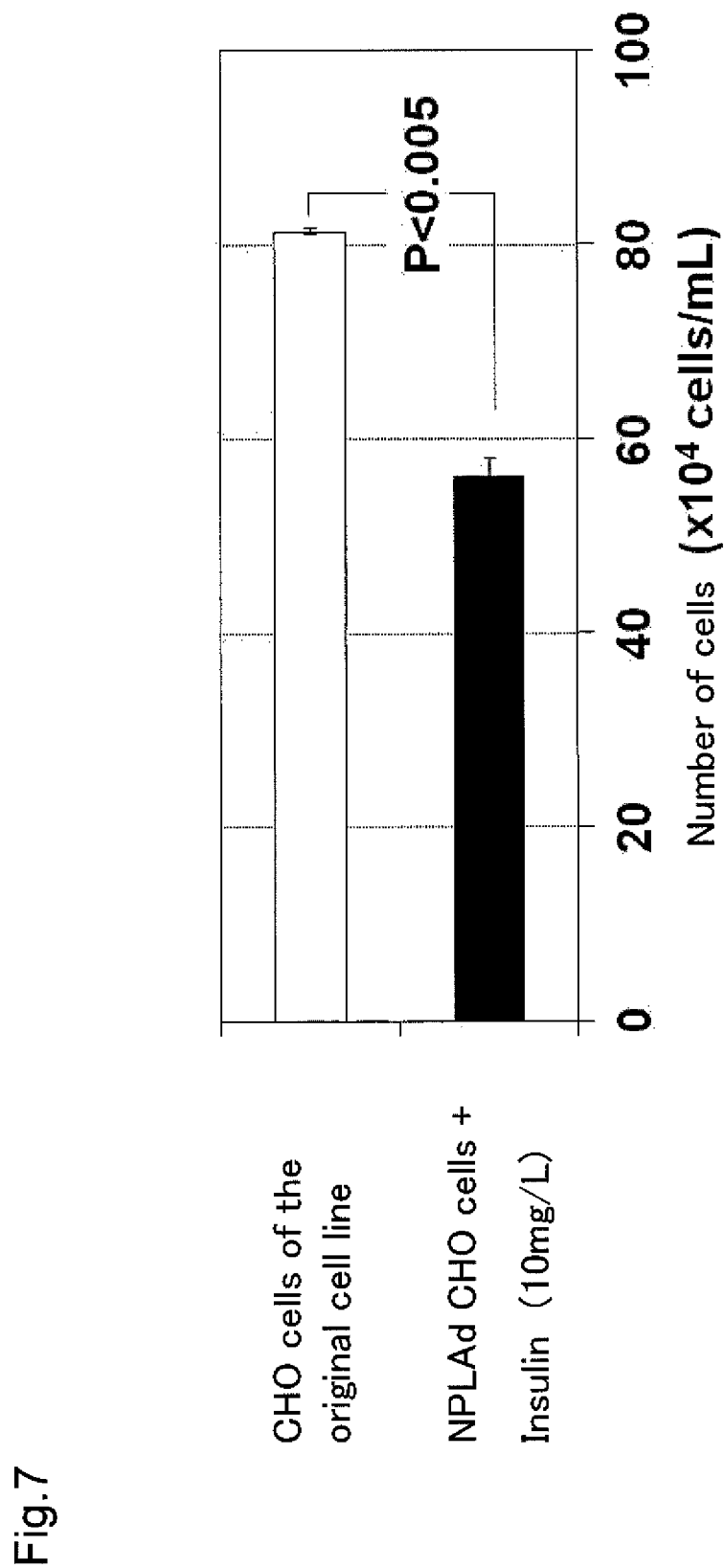
FIG. 7 is a figure that shows a comparison of cell proliferations between insulin-added NPLAd CHO cells and the original CHO cells. □: Original CHO cells; and ■: insulin-added (10 mg/L) NPLAd CHO cells. The numerical values are shown as an average (of three wells for each group)±SD.

The NPLAd CHO cells proliferated in an insulin concentration-dependent manner (-●-). The cell numbers were 400,000 cells/mL and 530,000 cells/mL at insulin concentrations of 2 mg/L and 10 mg/L, respectively. Thus, the cells were more than doubled at the insulin concentration of 10 mg/L compared to the cell number of the case where insulin was not added. It was studied to what extent the proliferation of the NPLAd CHO cells increases by adding insulin, as compared to the CHO cells of the original cell line. As a result, on the fifth day of culture, the NPLAd CHO cells in the NPL medium supplemented with 10 mg/L of insulin proliferated to about 550,000 cells/mL, whereas the cell number of the CHO cells of the original cell line was over 800,000 cells/mL ($P<0.005$) (FIG. 7). From this result, it was suggested that only by adding insulin to the NPL medium, the growth rate of the NPLAd CHO cells would not be comparable to that of the CHO cells of the original cell line. However, the effect of insulin to induce proliferation of the NPLAd CHO cells in a concentration-dependent manner was confirmed.

As stated above, it was found that the cell proliferation of the NPLAd CHO cell line increased depending on the concentration of the added insulin, which was a paracrine growth factor. Further, it was also found that the cell proliferation was inhibited by the anti-EGF neutralizing antibody even though no EGF was added to the medium. Furthermore, it was revealed that, in the cell proliferation induced by the stimulation of insulin, the cell proliferation was also suppressed by inhibiting EGF with the anti-EGF neutralizing antibody. Because no EGF was added to the medium, it was thought that EGF, of which binding to the receptor had been inhibited by the anti-EGF neutralizing antibody, was an autocrine growth factor produced by the adapted cell line per se, and that EGF induced the proliferation of the same cells from which it was secreted by forming an EGF/EGFR (receptor) autocrine loop.

Figure 8:
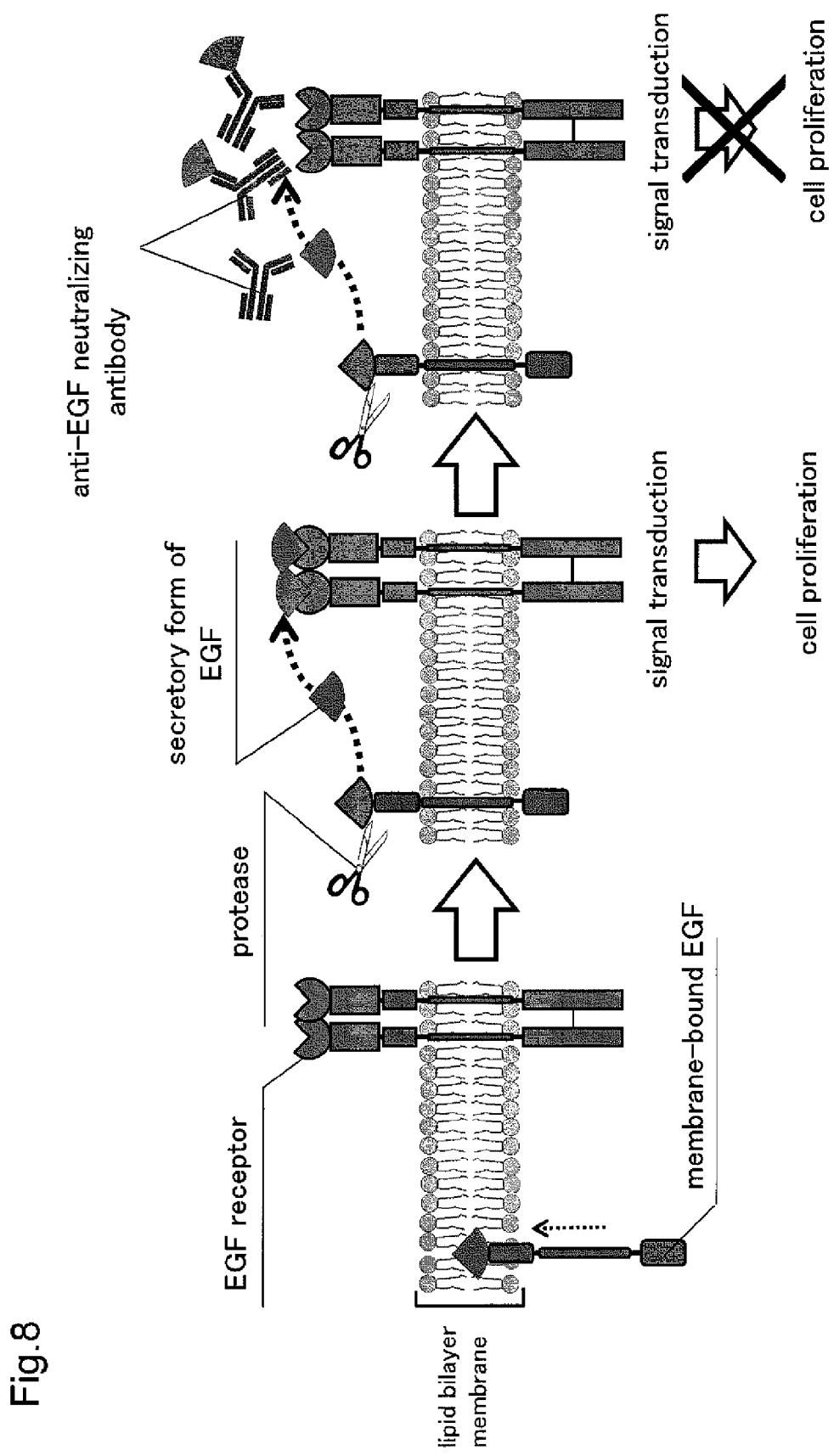
FIG. 8 is a schematic representation that shows the EGF/EGFR autocrine loop and inhibition of cell proliferation by an anti-EGF antibody.

EGF is a protein that is composed of fifty-three amino acid residues and has a molecular weight of 6,045 Da, and controls cell proliferation by binding to EGF receptors that are present on the surfaces of cells. It has been reported that EGF induces the self-proliferation of the cells as an autocrine growth factor in various cells including epidermal or epithelial cells by forming an EGF/EGFR autocrine loop (Shvartsman, et. al., Am J Physiol Cell Physiol., 2002; 282: C545-59; DeWitt, et. al., J Cell Sci., 2001; 114: 2301-13). Growth factors that belong to the EGF family including EGF per se are not synthesized as a secretory form, but are expressed as precursors in cells. After translation, the precursors come out of the cell surfaces by passing through the membranes. Thereafter, they are cut with a protease on the surfaces of cells to be growth factors of a secretory form. As shown in FIG. 8, EGF produced in a cell is present on the surface of a cell as a transmembrane protein (membrane-bound EGF) that is embedded in a cytoplasmic membrane. By being cleaved with a protease, the extracellular domain leaves the cell to be secretory EGF, which in turn binds to EGF receptor. By binding of secretory EGF to EGF receptor, the signal is transmitted to inside of the cell through the transmembrane domain of EGF receptor, and the cell proliferation is induced. The anti-EGF neutralizing antibody that was used in this study directly binds to EGF and inhibits the binding with the receptor. Therefore, as the reason that the cell proliferation of the adapted cell line was inhibited with the anti-EGF neutralizing antibody, it is inferred that the signal for proliferation from the receptor was not transmitted (FIG. 8). Further, in the adapted cell line according to the present invention, the anti-EGF neutralizing antibody inhibited not only self-proliferation but also the proliferation by insulin that is a paracrine growth factor. Therefore, in the adapted cell line, the autocrine production of EGF is a very important factor for proliferation of the cells themselves.

As described above, it was thought that the signal transduction of EGF was important for cell-proliferation in the adapted cell line. Therefore, hereinafter, it was studied whether the growth rate of the adapted cell line was able to be facilitated by increasing the signaling efficiency of EGF.

Among autocrine factors other than EGF, it has been reported that IGF-1 (Insulin-like Growth Factor-1) induced the proliferation of CHO cells (Pak, et. al., Cytotechnology, 1996; 22: 139-46). Therefore, using the NPLAd CHO cells, the binding of IGF-1 was inhibited by an anti-IGF-1 neutralizing antibody. However, the cell proliferation was not suppressed. Therefore, it was thought that IGF-1 was not responsible for the autocrine proliferation of the adapted cell line. However, from the result that the cell proliferation of the adapted cell line was not entirely suppressed by inhibition of binding using the anti-EGF neutralizing antibody, it is highly likely that an growth factor other than IGF-1 is responsible for the proliferation of the adapted cell line as an autocrine factor.

Figure 9:
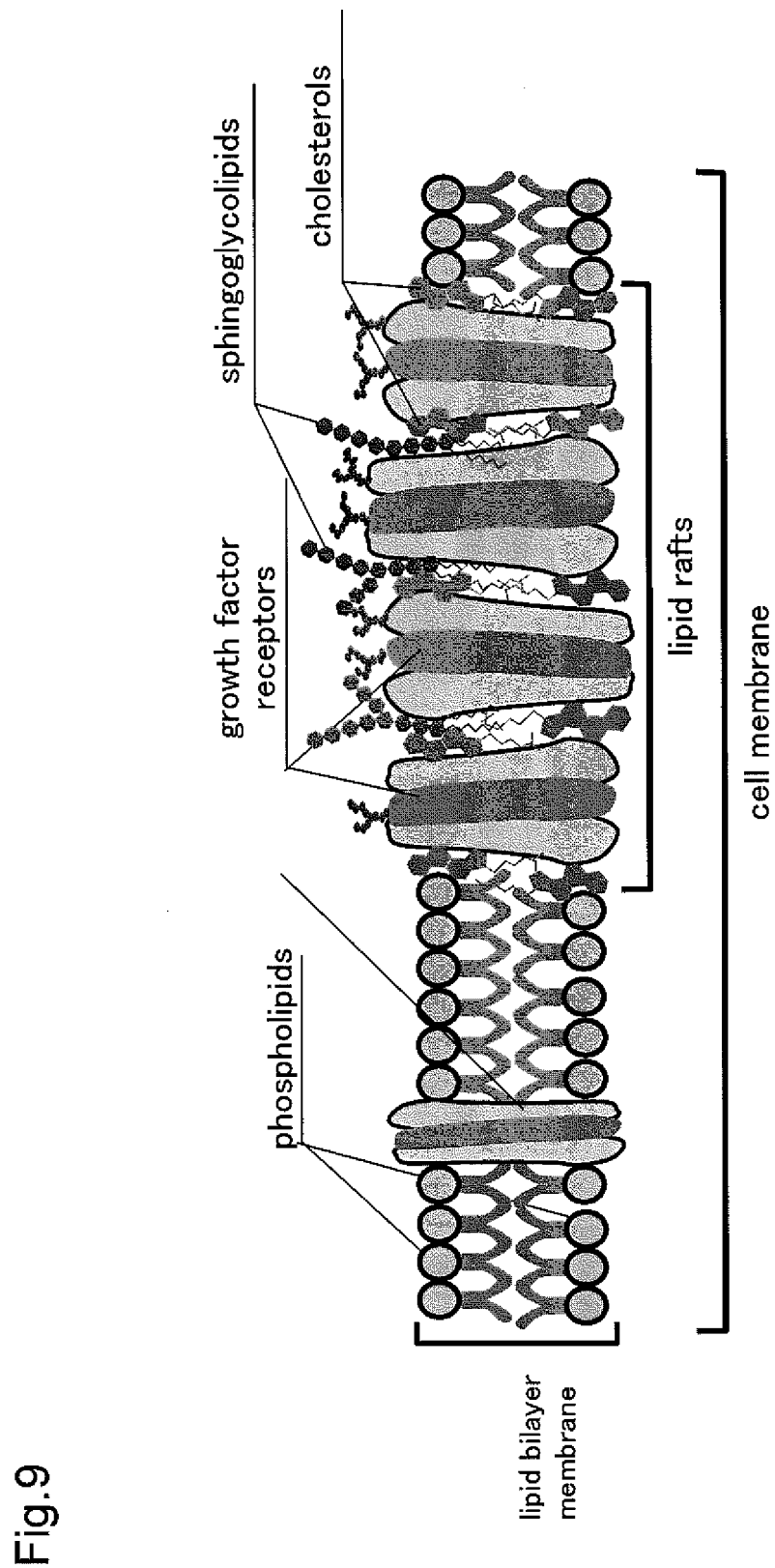
FIG. 9 is a schematic representation that shows the structure of cell membrane and lipid rafts.

5. Influence of GM3 on the Cell Proliferation of the CHO Cells Adapted to a Protein-Free and Lipid-Free Medium Cell membranes are constituted by a lipid bilayer that has been formed from an arrangement of a number of phospholipids such as, mainly, phosphatidylcholine, sphingomyelin, phosphatidylethanolamine, and phosphatidylserine, with various proteins (such as transmembrane proteins and anchor proteins) and the like, that are embedded in the lipid bilayer. The lipid rafts are structures of the membrane and comprise lipids, especially, sphingolipid, sphingoglycolipid, and cholesterol in large amounts. It is thought that the lipid rafts are involved in signal transductions to the inside of a cell (FIG. 9), because the transmembrane proteins as the receptors are concentrated in the lipid rafts. There are many reports that especially ganglioside, a sphingoglycolipid in a lipid raft, is responsible for the control of signal transductions. Further, it has been reported that the receptors for the EGF are localized in the lipid rafts (Balbis, et. al., J Cell Biochem., 2010; 109(6): 1103-8). Therefore, there is a possibility that the signal transductions via receptors are not fully functional if the formation of the lipid rafts is insufficient.

As described above, in the adapted cell line that had been continuously cultured in a protein-free and lipid-free medium for a long period of time, there is a possibility that its cell membrane structure has been altered due to the deficiency of lipids. Therefore, in the adapted cell line, there is a possibility that the formation of the lipid rafts is insufficient, and the signal transductions via EGF receptors are not fully functional. Thus, ganglioside GM3, a sphingoglycolipid, which plays an important role in the structure of the lipid raft, was noticed, and influences of the addition of GM3 to the cell morphology and growth rate of the adapted cells were studied. Namely, a possibility that the cell membrane structure is re-constructed and the cell adherent property is recovered by the addition of GM3, and another possibility that the presence or absence, or the concentration of GM3 results in alteration of the cell morphology, especially increase in the number of the adherent cells, or alteration of the size of the cell aggregates, were studied.

(1) Influence of GM3 on the Morphology of the CHO Cells Adapted to a Protein-Free and Lipid-Free Medium A commercially-available ganglioside GM3 (Neu5A, Enzo Life Science) was used. As the cells, the NPLAd CHO cells were used. The aggregated NPLAd CHO cells were suspended and dispersed in the NPL medium. Then, the number of the cells was counted by a dye-exclusion test by using the improved Neubauer hemocytometer and trypan blue, and the viability was calculated.

The NPLAd CHO cells were diluted to a cell number of 50,000 cells/mL with the NPL medium supplemented with insulin at a concentration of 10 mg/L. The entire cells were seeded at 1 mL/well in wells of 24-well plates. Then, to the plates containing the cells, ganglioside GM3 was added so as to be concentrations of 0, 250, 1,250, or 2,500 ng/mL.

The plates, on which the cells had been seeded, were incubated for five days under conditions of 37 degrees Celsius and 5% $CO_2$. Then, the alterations of the cell morphologies were observed with the inverted phase-contrast microscope. Thereafter, the numbers of the cells were respectively counted by a dye-exclusion test by using the improved Neubauer hemocytometer and trypan blue, and viabilities were respectively calculated. As the test to examine whether there was a significant difference, the Student's t-test was used.

(2) Comparison of the Growth Rate of the Insulin- and GM3-Added NPLAd CHO Cells to that of the CHO Cells of the Original Cell Line The NPLAd CHO cells and the CHO cells of the original cell line were used. Because the CHO cells of the original cell line were adherent, they were detached and suspended by using trypsin. Thereafter, the number of the cells was counted by a dye-exclusion test by using the improved Neubauer hemocytometer and trypan blue, and the viability was calculated. As for the NPLAd CHO cells, the cell aggregates were suspended and dispersed in the NPL medium. Thereafter, the number of the cells was counted by a dye-exclusion test by using the improved Neubauer hemocytometer and trypan blue, and the viability was calculated.

The CHO cells of the original cell line and the NPLAd CHO cells were diluted to a cell number of 50,000 cells/mL, with the DMEM medium supplemented with 10% FBS and the NPL medium supplemented with insulin at a concentration of 10 mg/L and GM3 at a concentration of 2,500 ng/mL, respectively. The entire cells were seeded at 1 mL/well in wells of 24-well plates. Then, the plates, on which the cells had been seeded, were incubated for five days under conditions of 37 degrees Celsius and 5% $CO_2$. At regular time intervals, the cell numbers were respectively counted by a dye-exclusion test by using the improved Neubauer hemocytometer and trypan blue, and the viabilities were respectively calculated. As the test to examine whether there was a significant difference, the Student's t-test was used.

(3) Results

Figure 10:
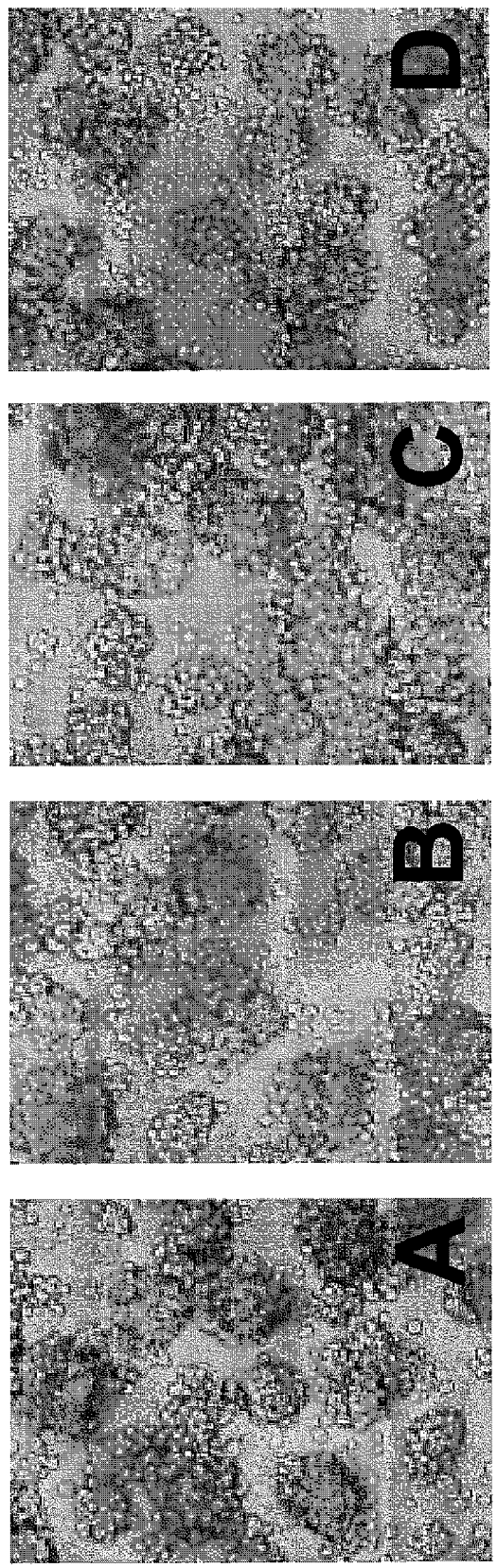
FIG. 10 is an inverted phase-contrast microphotograph (40 magnifications) which shows influences of the addition of ganglioside GM3 to the cellular morphologies. Panel A: 0 ng/mL GM3; Panel B: 250 ng/mL GM3; Panel C: 1,250 ng/mL GM3; and Panel D: 2,500 ng/mL GM3.

FIG. 10 shows the result of observation about the alteration of cell morphologies by the addition of GM3. Irrespective of the presence or absence, or the concentration of added GM3, alteration of cell morphologies, such as increase in the number of adherent cells or alteration of the size of the cell aggregates, was not observed.

Figure 11:
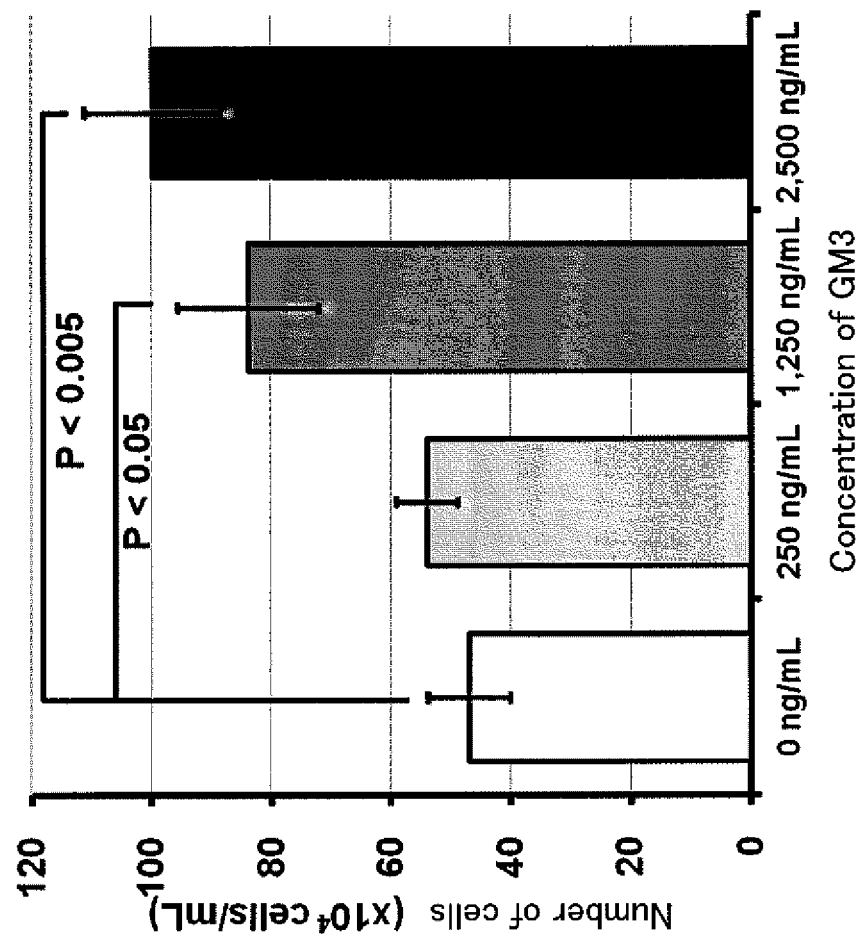
FIG. 11 is a figure that shows influences of the amount of added ganglioside GM3 on cell proliferation. The numerical values are shown as an average (of three wells for each group) ±SD.

FIG. 11 shows the result of influence on the cell proliferation by the addition of GM3. In the case where GM3 was added at a concentration of 1,250 ng/mL to the culture medium for the NPLAd CHO cells, the cell number was significantly increased ($P<0.05$) as compared to the case where GM3 was not added. This effect was GM3 concentration-dependent. In the case where GM3 was added at a concentration of 2,500 ng/mL, the cell number increased to about 1,000,000 cells/mL, which was about twice of the case where GM3 was not added. Therefore, it was revealed that GM3 had an effect to induce cell proliferation of the NPLAd CHO cells.

Figure 12:
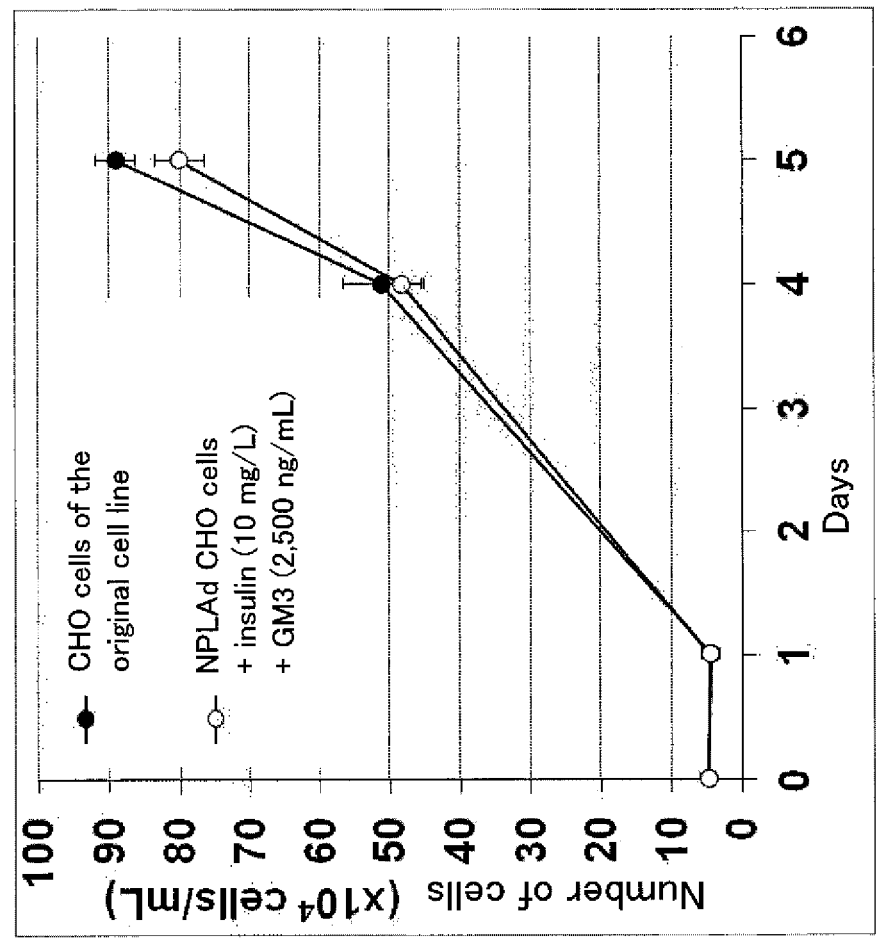
FIG. 12 is a figure that shows a comparison of cell proliferations between NPLAd CHO cells that have been cultured in an insulin- and GM3-added NPL medium, and the original CHO cells that have been cultured in a serum-added medium. -○-: NPLAd CHO cells that have been cultured in an insulin- and GM3-added NPL medium; and -●-: original CHO cells that have been cultured in a serum-added medium. The numerical values are shown as an average (of three wells for each group)±SD.

Next, the facilitation of proliferation by the addition of insulin and GM3 was studied. FIG. 12 shows the results. In the case where insulin (10 mg/L) and GM3 (2,500 ng/mL) were added to the NPL medium, the NPLAd CHO cells (-○-) showed a cell growth rate that is about the same as that of the CHO cells (-●-) of the original cell line in a medium supplemented with serum. Therefore, it was shown that, by adding insulin and GM3 to a medium, the NPLAd CHO cells showed a growth rate that was comparable to that of the CHO cells.

As described above, the proliferation of the NPLAd CHO cells was induced by adding GM3. Further, by using GM3 in combination with insulin, its growth rate increased to an extent similar to that of the CHO cells of the original cell line, in a static culture as well. Meanwhile, any change in the cell morphology was not observed. Therefore, it is thought that the deficiency of GM3 is not responsible for the ability of cells to be suspended.

It has been said that GM3 is responsible for the signal transduction of a cell, as well as that it is a major structural component of lipid rafts. However, as for the participation of GM3 to the signal transduction, there are contradictory reports that GM3 acts both suppressively and inducibly. Bremer, et. al., reported that the GM3 was a modulator of EGF receptor because, in A431 cells and KB cells overexpressing EGF receptors, addition of exogenous GM3 modulated the signal transduction by inhibiting the autophosphorylation of tyrosine kinase of EGF receptor, and inhibited EGF-dependent cell proliferation (Bremer, et. al., J Biol. Chem., 1986; 261: 243440). Whereas, Ji, et al., reported, using the same A431 cells, that the autophosphorylation of tyrosine kinase of EGF receptor was reduced by removing ganglioside on the cell surface with an endoglycoceramidase that was able to cleave sphingoglycolipid on the surface of a living cell under physiological conditions (Ji, et al., Glycobiology, 1995; 5: 343-50). Further, there is also a report that activities of tyrosine kinase of not only EGF receptor but also growth factors such as FGF, IGF-1 and PDGF, as well as their receptors, were inhibited, and thus the proliferation was inhibited by removing gangliosides with a glycosylceramide synthesis inhibitor, D-PPPP hydrochloride (D-1-threo-1-phenyl-2-hexadecanoylamino-3-pyrrolidino-1-propanol-HCl), in Swiss 3T3 fibroblast cells, but the inhibition was cancelled and proliferation was restored by adding exogenous gangliosides (Li, et al., J Biol. Chem., 2000; 275: 34213-23). From the above reports that are seemingly contradictory, it has been thought that gangliosides are a factor that is essential for the expressions of the functions of growth factors and receptors, and particularly the functions of receptors for various growth factors are deteriorated by deficiency of gangliosides, and, on the other hand, that the addition of exogenous GM3 to a cell line overexpressing EGF receptors acts to inhibit the functions. In recent studies about diabetes mellitus, there are reports that the elevated synthesis of GM3 due to the stimulation with TNF-α causes a functional abnormality of lipid rafts and suppresses selectively the metabolic signal of insulin (Tagami, et al., J Biol Chem., 2002; 277: 30855-92; Inoguchi, Himan-kenkyu (obesity research), 2006; 12: 260-2). It shows that excessive GM3 causes insulin resistance. It is thought from these facts that although GM3 in an amount that is necessary to form lipid rafts acts facilitatively, whereas excessive GM3 acts suppressively, to proliferation.

Figure 13:
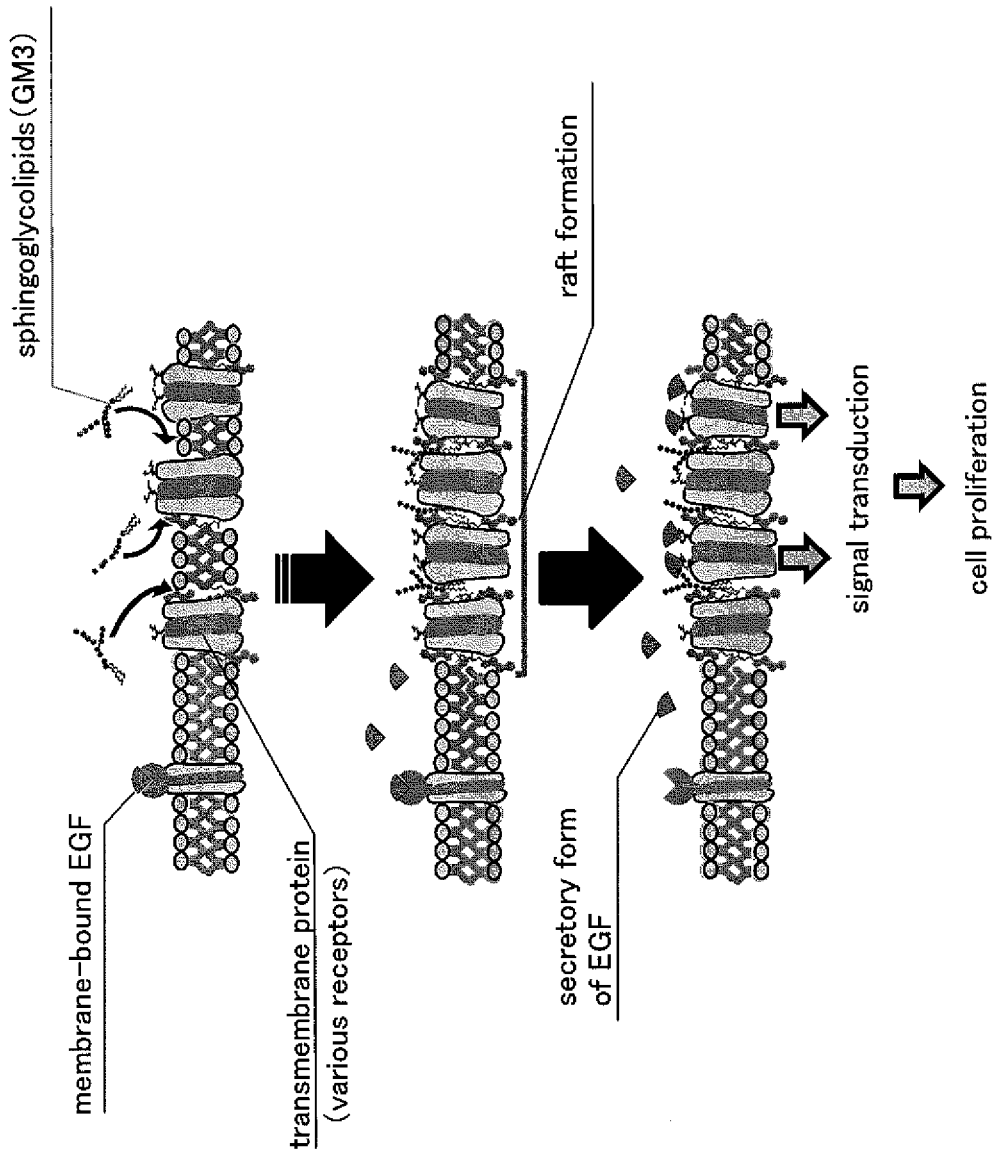
FIG. 13 is a schematic representation of a concept of induction of lipid raft formation by the addition of GM3.

The cell line adapted to a protein-free and lipid-free medium according to the present invention is exposed for a long period of time to a state that is deficient for lipids, especially gangliosides. Therefore, there is a possibility that the receptors on lipid rafts have been affected. It is thought that, in the adapted cell line under a lipid-deficient condition, the functions of receptors on lipid rafts is normalized by adding GM3, which act in the direction of inducing proliferation (FIG. 13).

Figure 14:
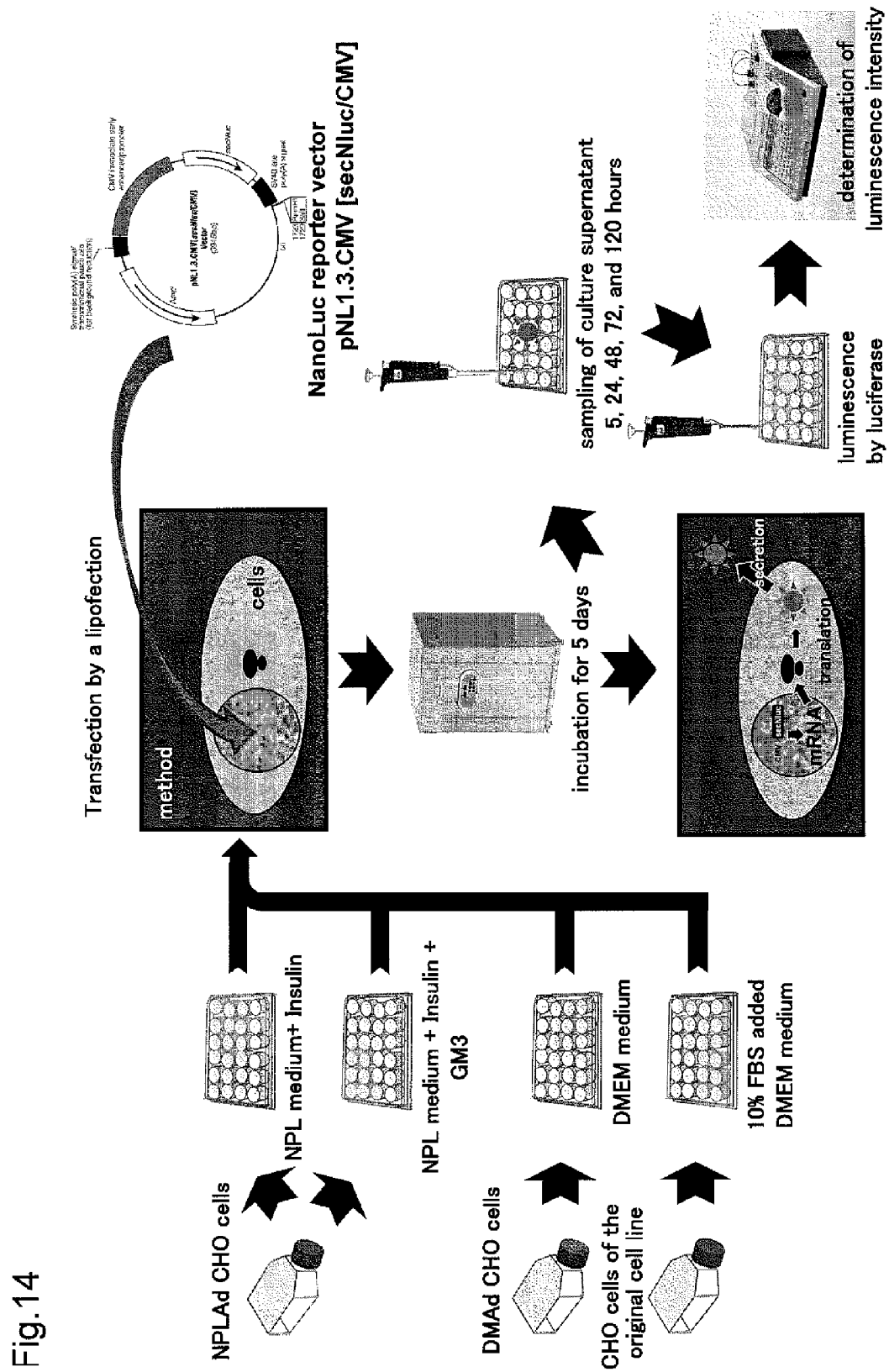
FIG. 14 is a schematic representation that shows a flow of an experiment for comparing productivities of a recombinant protein by a transient assay of the original CHO cells and of cells of an adapted cell line.

6. Production of Recombinant Proteins in CHO Cells Adapted to a Protein-Free and Lipid-Free Medium A transient method was used for verifying a production system of a substance. The productive capacity of a recombinant protein of the cells of the CHO cell line adapted to a protein-free and lipid-free medium was studied as compared to that of the CHO cells of the original cell line, according to the procedures shown in FIG. 14 by using the expression of secretory luciferase as an index.

(1) Experimental Procedures (1-1) Transfection of Expression Vector Carrying a Gene of Secretory Luciferase The CHO cells of the original cell line were cultured in a DMEM medium supplemented with 10% FBS. The DMAd CHO cells were cultured in a DMEM medium. The NPLAd CHO cells were cultured either in an NPL medium supplemented with insulin (10 mg/L) or in an NPL medium supplemented with insulin (10 mg/L) and GM3 (2,500 ng/mL).

Figure 15:
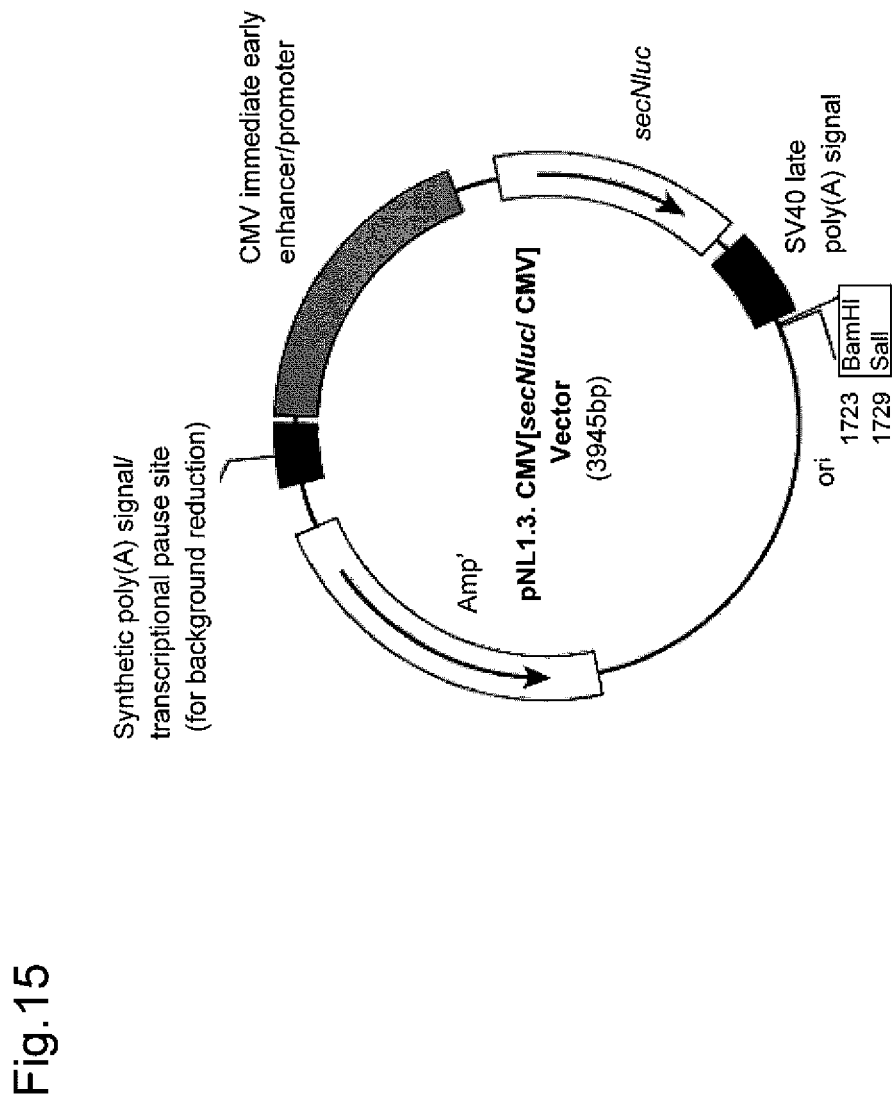
FIG. 15 is a vector map of NanoLuc reporter vector pNL1.3.CMV.

The "TransIT-LT1 Transfection Regent" (by Takara, MIR2304) as a transfection reagent and the "NanoLuc® reporter vector pNL1.3. CMV [secNluc/CMV]" (by Promega, N1101) as an expression vector carrying a gene of secretory luciferase, were respectively used (FIG. 15).

The CHO cells of the original cell line were detached by using trypsin and washed twice with the DMEM medium supplemented with 10% FBS. After washing, the number of the cells was counted by a dye-exclusion test by using the improved Neubauer hemocytometer and trypan blue, and the viability was calculated. The DMAd CHO cells were washed with the DMEM medium, and the NPLAd CHO cells were washed with the NPL medium supplemented with insulin (10 mg/L) or NPL medium supplemented with insulin (10 mg/L) and GM3 (2,500 ng/mL). Then, the cell aggregates were suspended and dispersed in each of the media. Thereafter, the numbers of the cells were counted by a dye-exclusion test by using the improved Neubauer hemocytometer and trypan blue, and the viabilities were calculated.

After the viabilities of 90% or more were confirmed, the cell number was respectively adjusted to 400,000 cells/mL in each of the media. The cells were seeded in wells of the 24-well plate at 0.5 mL/well. The plates, on which the cells had been seeded, were incubated for twenty-four hours under conditions of 37 degrees Celsius and 5% $CO_2$.

To 700 μl, of the DMEM medium, 7 μL of 1 μg/μL of the "NanoLuc® reporter vector pNL1.3 CMV" was added and mixed. Then, the "TransIT-LT1 Transfection Regent," 21 μL, was added and mixed. The mixture was kept standing at room temperature for thirty minutes to allow a transfection complex being prepared. As a control, a dummy complex was prepared in the same manner, except that TE buffer had been added instead of the "NanoLuc® reporter vector pNL1.3. CMV."

The prepared transfection complex, 52 μL/well, was added dropwise to the wells of the plates, on which the cells had been seeded. For one combination of the cell and the medium, three wells were used. By gently rocking the plates, the contents in each well were mixed. The dummy complex was added dropwise to the wells of the plates and the contents in each well were mixed in the same manner (one well per combination of the cell and the medium). The plates were incubated for five days under conditions of 37 degrees Celsius and 5% $CO_2$.

Hereinafter, the NPLAd cells that were obtained by culturing in an NPL medium supplemented with insulin (10 mg/L) and then being transfected, and the NPLAd cells that were obtained by culturing in an NPL medium supplemented with insulin (10 mg/L) and GM3 (2,500 ng/mL) and then being transfected, will be respectively referred to as "NPLAd CHO cells without GM3" and "NPLAd CHO cells with GM3."

(1-2) Assay of the Specific Activity of Luciferase

The "Nano-Glo Luciferase Assay System" (by Promega, N1110) was used as a luciferase assay kit.

From each well of the plates, into which the cells were seeded and the transfection was completed, 10 μL of supernatant was taken 5, 24, 48, 72, and 120 hours after the completion of the transfection. The activity of secretory luciferase contained in the supernatant was assayed using the "Nano-Glo Luciferase Assay System" with a luminometer.

(1-3) Calculation of the Specific Activity of Luciferase

The specific activity of luciferase is the ratio of the luminescence of the supernatant of the adapted cell line under each incubation condition to that of the supernatant of the CHO cells of the original cell line, in which the supernatants were sampled at the same time. The calculation was carried out as follows:

[Mathematical Formula 1]
(1) the Specific Activity of Luciferase (%) of DMAd CHO Cells {[(average luminescence intensity of transfected DMAd CHO cells)−(luminescence intensity of dummy DMAd CHO cells−blank)]/[(average luminescence intensity of transfected CHO cells of the original cell line)−(luminescence intensity of dummy CHO cells of the original cell line−blank)]}×100

(2) The Specific Activity of Luciferase (%) of NPLAd CHO Cells to which GM3 was not Added {[(average luminescence intensity of transfected NPLAd CHO cells without GM3)−(luminescence intensity of dummy NPLAd CHO cells without GM3−blank)]/[(average luminescence intensity of transfected CHO cells of the original cell line)−(luminescence intensity of dummy CHO cells of the original cell line−blank)]}×100

(3) The Specific Activity of Luciferase (%) of NPLAd CHO Cells to which GM3 was Added {[(average luminescence intensity of transfected NPLAd CHO cells with GM3)−(luminescence intensity of dummy NPLAd CHO cells with GM3−blank)]/[(average luminescence intensity of transfected CHO cells of the original cell line)−(luminescence intensity of dummy CHO cells of the original cell line−blank)]}×100

The experiment was repeated three times, and the data were shown as the average of specific activities of luciferase of all experiments±SD. As the test to examine whether there was a significant difference, the Student's t-test was used.

(1-4) Comparison of Luminescence Per Cell

To compare the luminescence for each group of cells, the luminescence of the supernatants, which were sampled with time after transfection, of each group of cells was divided by the number of cells increased in a period, of the same time, the same cell, the same composition of the medium, and the same incubation conditions. Namely, the luminescence per cell was presumptively calculated.

(2) Results

Figure 16:
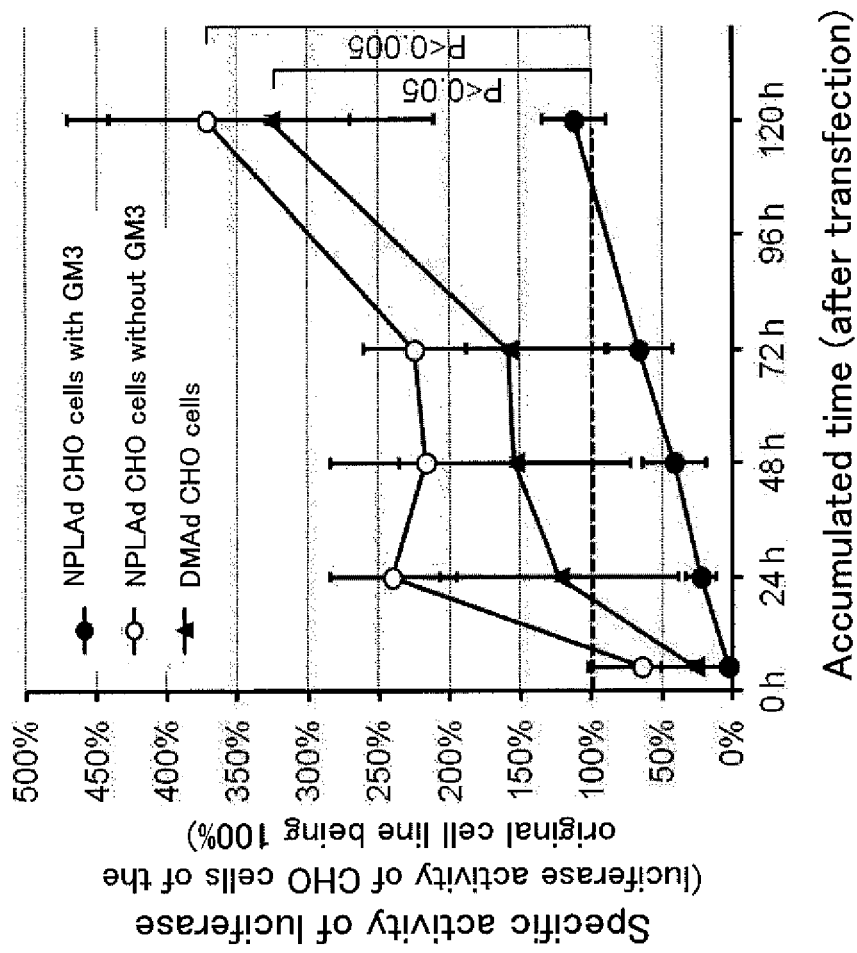
FIG. 16 is a figure that shows a comparison among specific activities of luciferase of the DMAd CHO cells, the GM3-added NPLAd CHO cells, and the NPLAd CHO cells with no added GM3, based on the luciferase activity of the original CHO cells. -▲-: DMAd CHO cells; -○-: NPLAd CHO cells with no added GM3; and -●-: GM3-added NPLAd CHO cells. The numerical values are shown as an average (of specific activities of luciferase of three experiments for each experiment group)±SD.

To study the protein productivity of the adapted cell line, the cells were transfected by a lipofection method with plasmid pNL1.3.CMV vector, carrying cDNA of secretory luciferase integrated downstream of the CMV promoter, and the activities of luciferase that had been respectively secreted into media of the CHO cells of the adapted cell line and the CHO cells of the original cell line were compared by assaying the luminescence. FIG. 16 shows the results. In the NPLAd CHO cells with GM3, the protein yield just after transfection was slowly increased. However, after 120 hours, there was no significant difference between the specific activities of luciferase of the CHO cells of the original cell line and the NPLAd CHO cells with GM3. The overall protein yield of the NPLAd CHO cells with GM3 (-●-) was comparable to that of the CHO cells of the original cell line. The DMAd CHO cells (-▲-) and the NPLAd CHO cells without GM3 (-○-) showed specific activities of luciferase, which were three times or more of that of the CHO cells of the original cell line, at 120 hours after the transfection. The significant differences were $p<0.05$ and $p<0.005$ for the DMAd CHO cells and the NPLAd CHO cells without GM3, respectively. Therefore, it was thought that the protein productivities of the established cell lines were higher than that of the CHO cells of the original cell line.

Figure 17:
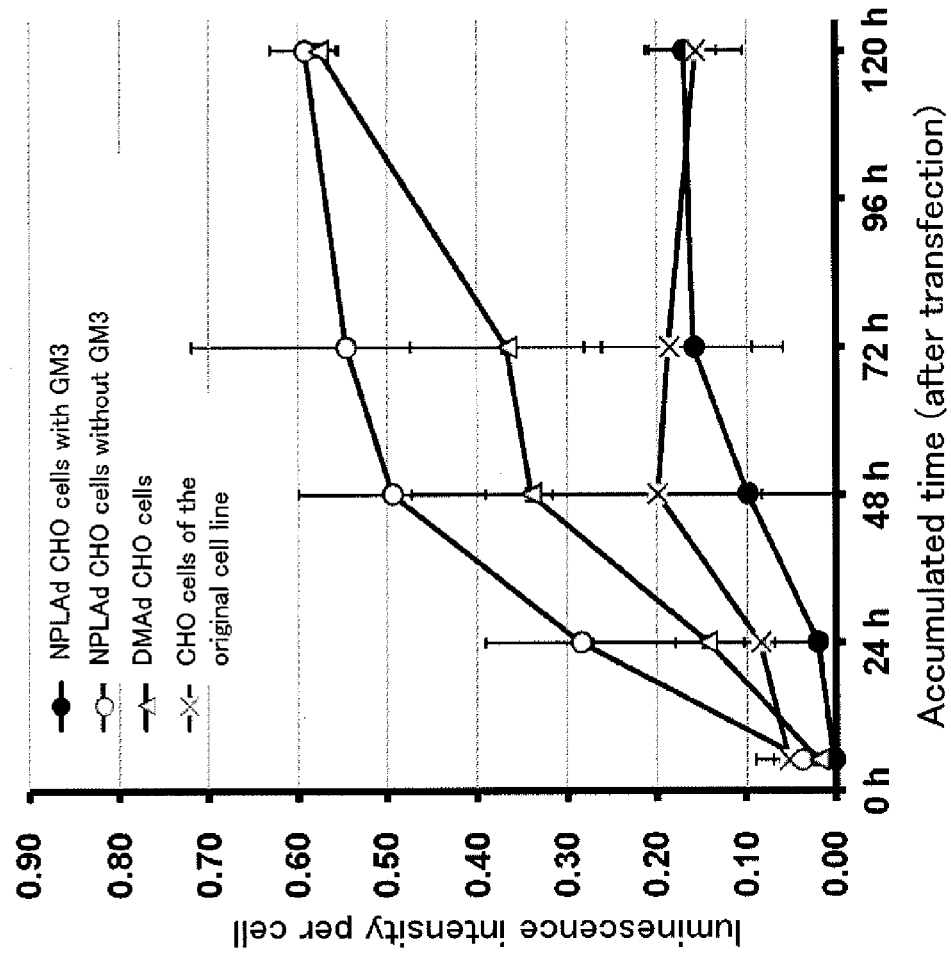
FIG. 17 is a figure that shows a comparison among estimated values of the luciferase activities per cell of the GM3-added. NPLAd CHO cells, the NPLAd CHO cells with no added GM3, the DMAd CHO cells, and the original CHO cells. -●-: GM3-added NPLAd CHO cells; -○-: NPLAd CHO cells with no added GM3; -Δ-: DMAd CHO cells; and -X-: the original CHO cells. The numerical values are the total luminescence of each cell group determined in FIG. 16 divided by the number of cells in the cell group with time, wherein the number of cells are determined by culturing the cells in the same medium under the same culturing conditions, and are shown as an average±SD.

To convert the data into luminescence per cell, the luminescence with time that was assayed in FIG. 16 was divided by the number of increased cells, for the same time point, the same cell, the same composition of the medium, and the same incubation conditions, thereby the luminescence per cell was presumptively calculated (FIG. 17). As a result, it was estimated that, at 120 hours after the transfection, the luminescence per cell of the DMAd CHO cells (-Δ-) was almost the same as that of the NPLAd CHO cells without GM3 (-○-), and was about four times that of the CHO cells of the original cell line (-X-). Further, it was estimated that, at 120 hours after the transfection, the luminescence per cell of the NPLAd CHO cells with GM3 (-●-) was almost the same as that of the CHO cells of the original cell line.

From these results, it was shown that each of the adapted cell lines was able to produce a recombinant protein at a productivity that is similar to or more than that of the CHO cells of the original cell line. The DMAd CHO cells and the NPLAd CHO cells without GM3 produced three times or more of luciferase as compared to luciferase produced by the CHO cells of the original cell line (FIG. 16). Further, when the luciferase activity per cell was estimated, at 120 hours after the transfection, the activities of the DMAd CHO cells and the NPLAd CHO cells without GM3 were four times higher than that of the CHO cells of the original cell line, and the activity of the NPLAd CHO cells with GM3 was almost the same as that of the CHO cells of the original cell line (FIG. 17).

The reason why the adapted cell lines show higher luciferase productivities than that of the CHO cells of the original cell line is not clearly understood. However, there is a possibility that alteration of the membrane structures of the adapted cell lines influenced. As described above, there is a possibility that, because the adapted cell lines were exposed to a condition of lipid-deficiency for a long period of time by passages in protein-free and lipid-free media, the structures of their cell membranes altered and thereby their transfection efficiencies were elevated. Further, there is another possibility that membrane permeability was increased for proteins synthesized in cells, and thus more luciferase protein was secreted.

From these results, it was demonstrated that an efficient production of a recombinant protein was able to be realized by ensuring a sufficient number of cells in culture before transfection by adding insulin and GM3 to a medium, and then transfecting the cells by a transient method after removing GM3.

What is claimed is:

1. A method for producing a recombinant protein comprising:
   (a) culturing a transformed cell in a protein-free and lipid-free medium comprising no exogenous growth factors, wherein the transformed cell was produced by transfecting a cell of a cell line derived from Chinese Hamster Ovary (CHO) cells with a vector comprising a gene coding for the recombinant protein to be produced under the control of a promoter operable in the cell, and
   wherein the cell line is adapted to a protein-free and lipid-free medium, and is able to proliferate in a suspended state in the protein-free and lipid-free medium comprising no exogenous growth factors without altering a growth rate and cell morphologies for at least three passages, and
   (b) recovering the recombinant protein produced by the transformed cell.

2. The method as described in claim 1, wherein the cell line has been deposited under Accession number NITE BP-01641.

3. The method as described in claim 1, wherein the protein-free and lipid-free medium used in the culturing the transformed cell is a medium comprising putrescine, thymidine, hypoxanthine, and monoethanolamine, in a modified DMEM medium that is modified from DMEM so as to contain glucose at a concentration 3 to 5 times the usual concentration and to contain no exogenous growth factors.

4. The method as described in claim 3, wherein the protein-free and lipid-free medium comprises 2000 to 5000 mg/L of glucose, 0.001 to 2 mg/L of putrescine, 0.01 to 1 mg/L of thymidine, 0.1 to 10 mg/L of hypoxanthine, and 0.1 to 5 mg/L of monoethanolamine.

5. The method as described in claim 1, wherein the protein-free and lipid-free medium used in the culturing the transformed cell comprises 1 to 20 mg/L of insulin and/or 0.1 to 10 mg/L of ganglioside GM3.

6. The method as described in claim 1, wherein the transformed cell had been cultured in a protein-free and lipid-free medium comprising insulin and ganglioside GM3 before it was subjected to transformation.

7. The method as described in claim 1, wherein the transformed cell had been cultured in a protein-free and lipid-free medium comprising insulin and ganglioside GM3, and thereafter subjected to transfection in a protein-free and lipid-free medium comprising no GM3.

8. The method as described in claim 2, wherein the protein-free and lipid-free medium used in the culturing the transformed cell comprises putrescine, thymidine, hypoxanthine, and monoethanolamine, in a modified DMEM medium that is modified from DMEM so as to contain glucose at a concentration 3 to 5 times the usual concentration and to contain no exogenous growth factors.

9. The method as described in claim 2, wherein the protein-free and lipid-free medium used in the culturing the transformed cell comprises 1 to 20 mg/L of insulin and/or 0.1 to 10 mg/L of ganglioside GM3.

10. The method as described in claim 3, wherein the protein-free and lipid-free medium used in the culturing the transformed cell comprises 1 to 20 mg/L of insulin and/or 0.1 to 10 mg/L of ganglioside GM3.

11. The method as described in claim 4, wherein the protein-free and lipid-free medium used in the culturing the transformed cell comprises 1 to 20 mg/L of insulin and/or 0.1 to 10 mg/L of ganglioside GM3.

12. The method as described in claim 2, wherein the transformed cell had been cultured in a protein-free and lipid-free medium comprising insulin and ganglioside GM3 before it was subjected to transformation.

13. The method as described in claim 3, wherein the transformed cell had been cultured in a protein-free and lipid-free medium comprising insulin and ganglioside GM3 before it was subjected to transformation.

14. The method as described in claim 4, wherein the transformed cell had been cultured in a protein-free and lipid-free medium comprising insulin and ganglioside GM3 before it was subjected to transformation.

15. The method as described in claim 5, wherein the transformed cell had been cultured in a protein-free and lipid-free medium comprising insulin and ganglioside GM3 before it was subjected to transformation.

16. The method as described in claim 2, wherein the transformed cell had been cultured in a protein-free and lipid-free medium comprising insulin and ganglioside GM3, and thereafter subjected to transfection in a protein-free and lipid-free medium comprising no GM3.

17. The method as described in claim 3, wherein the transformed cell had been cultured in a protein-free and lipid-free medium comprising insulin and ganglioside GM3, and thereafter subjected to transfection in a protein-free and lipid-free medium comprising no GM3.

18. The method as described in claim 4, wherein the transformed cell had been cultured in a protein-free and lipid-free medium comprising insulin and ganglioside GM3, and thereafter subjected to transfection in a protein-free and lipid-free medium comprising no GM3.

19. The method as described in claim 5, wherein the transformed cell had been cultured in a protein-free and lipid-free medium comprising insulin and ganglioside GM3, and thereafter subjected to transfection in a protein-free and lipid-free medium comprising no GM3.

20. The method as described in claim 6, wherein the transformed cell had been cultured in a protein-free and lipid-free medium comprising insulin and ganglioside GM3, and thereafter subjected to transfection in a protein-free and lipid-free medium comprising no GM3.

* * * * *